United States Patent
Kamal et al.

(10) Patent No.: US 8,835,421 B2
(45) Date of Patent: Sep. 16, 2014

(54) BENZIMIDAZOLE LINKED PYRROLO[2,1-C[1,4] BENZODIAZEPINE HYBRIDS AS POTENTIAL ANTITUMOUR AGENTS AND PROCESS FOR THE PREPARATION THEREOF

(75) Inventors: Ahmen Kamal, Hyderabad (IN); Pogula Praveen Kumar, Hyderabad (IN); Bobburi Naga Seshadri, Hyderabad (IN); Kokkonda Sreekanth, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 426 days.

(21) Appl. No.: 12/921,594

(22) PCT Filed: Oct. 31, 2008

(86) PCT No.: PCT/IN2008/000718
§ 371 (c)(1),
(2), (4) Date: Apr. 25, 2011

(87) PCT Pub. No.: WO2009/113085
PCT Pub. Date: Sep. 17, 2009

(65) Prior Publication Data
US 2011/0190268 A1 Aug. 4, 2011

(30) Foreign Application Priority Data
Mar. 11, 2008 (IN) .............................. 603/DEL/2008

(51) Int. Cl.
*A61K 31/5517* (2006.01)
*C07D 243/06* (2006.01)
*C07D 403/12* (2006.01)

(52) U.S. Cl.
CPC .......... *C07D 403/12* (2013.01); *A61K 31/5517* (2013.01); *C07D 243/06* (2013.01)
USPC ....... 514/211.04; 514/217; 540/496; 540/586

(58) Field of Classification Search
CPC ... A61P 35/00; A61K 31/5517; C07D 243/06
USPC ..................... 514/211.04, 217; 540/496, 586
See application file for complete search history.

(56) References Cited

FOREIGN PATENT DOCUMENTS

WO    WO 2005/063759    7/2005

OTHER PUBLICATIONS

W. A. Denny et al., "Potential Antitumor Agents. 59. Structure-Activity Relationships for 2-Phenylbenzimidazole-4-Carboxamides, a New Class of "Minimal" DNA-Intercalating Agents witch May Not Act via Topoisomerase II," J. Med. Chem. 33(2):814-819, Feb. 1990.

(Continued)

*Primary Examiner* — Brenda Coleman
(74) *Attorney, Agent, or Firm* — Lathrop & Gage LLP

(57) ABSTRACT

The present invention provides a compounds of general formula (8), (11) and (14), useful as potential antitumour agents against human cancer cell lines. The present invention further provides a process for the preparation of pyrrolo[2,1-c][1,4] benzodiazepine hybrids of general formula (8), (11) and (14).

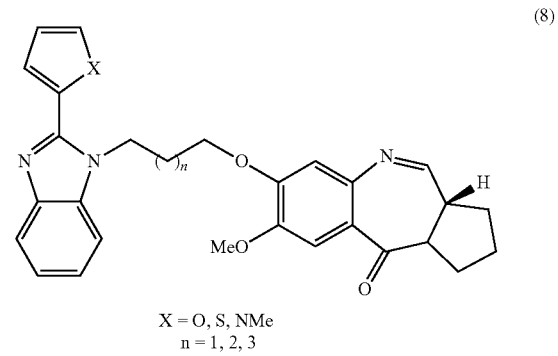

X = O, S, NMe
n = 1, 2, 3

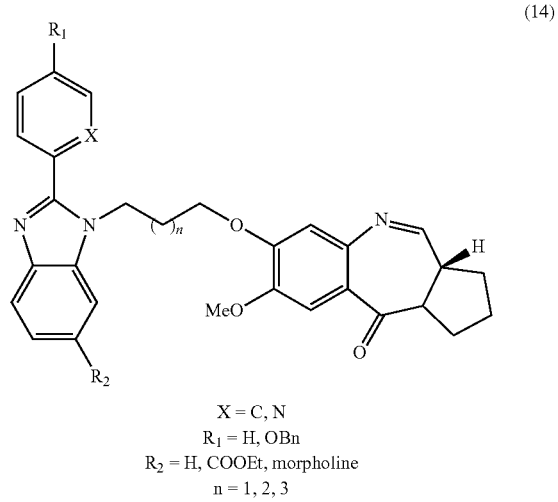

X = C, N
$R_1$ = H, OBn
$R_2$ = H, COOEt, morpholine
n = 1, 2, 3

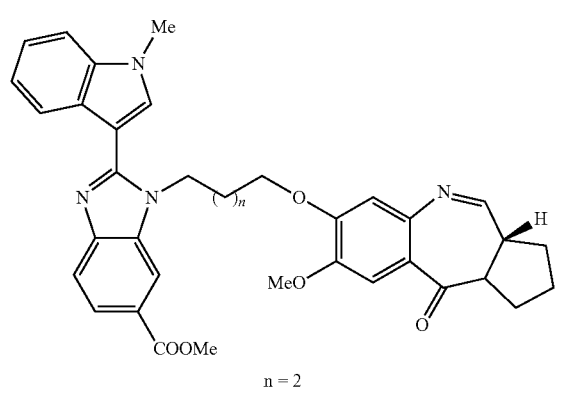

n = 2

14 Claims, No Drawings

(56) References Cited

OTHER PUBLICATIONS

P. B. Dervan, "Design of Sequence-Specific DNA-Binding Molecules," Science 232:464-471, Apr. 25, 1986.
S. Foister et al., "Shape Selective Recognition of T•A Base Pairs by Hairpin Polyamides Contaniing N-Terminal 3-Methoxy (and 3-Chloro)Thiophene Residues," Bioorg. Med. Chem. 11:4333-4340, 2003.
S. J. Gregson et al., "Design, Synthesis, and Evaluation of A Novel Pyrrolobenzodiazepine DNA-Interactive Agent with Highly Efficient Cross-Linking Ability and Potent Cytotoxicity," J. Med. Chem. 44(5):737-748, Web Release Jan. 31, 2001.
S. S. Hecht et al., "On the Structure and Carcinogenicity of the Methylchrysenes," Carcinogenesis 1:325-340, 1976.
L. H. Hurley, "DNA and Associated Targets for Drug Design," J. Med. Chem. 32(9):2027-2033, Sep. 1989.
L. H. Hurley, "Pyrrolo(1,4)benzodiazepine Antitumor Antibiotics. Comparative Aspects of Arythramycin, Tomaymycin and Sibiromycin," J. Antibiot. 30:349-370, May 1977.
L. H. Hurley et al., "Pyrrolo(1,4)benzodiazepine antitumor antibiotics in vitro interaction of anthramycin, sibiromycin and tomaymycin with DNA using specifically radiolabelled molecules," Biochem. Biophys. Acta 475:521-535, 1977.
International Search Report for WO 2009/113085, International Application No. PCT/IN2008/000718, Feb. 17 2009, 3 pages.
Y.-H. Ji et al., "Tris-Benzimidale Derivatives: Design, Synthesis and DNA Sequence Recognition," Bioorg. Med. Chem. 9:2905-2919, 2001.
A. Kamal et al., "A New Route for the Synthesis of Pyrrolo[2,1-c][1,4]benzodiazepine Antibiotics via Oxidation of Cyclic Secondary Amine," Chem. Commun. 385-386, 1996.
A. Kamal et al., "Synthesis of Pyrrolo[2,1-c][1,4]benzodiazepine Antibiotics via Azido Reductive Cyclization with HMDST," Tetrahedron Letters 37(37):6803-6806, Sep. 9, 1996.
A. Kamal et al., "Design, Synthesis and Evaluation of New Noncross-Linking Pyrrolobenzodiazepine Dimers with Efficient DNA Binding Ability and Potent Antitumor Activity," J. Med. Chem. 45(21):4679-4688, Web Release Sep. 17, 2002.
A. Kamal et al. "Synthesis and DNA Binding Affinity of Novel *A*-C8/*C*-C2-exo Unsaturated Alkoxyamino-Linked Pyrrolo[2,1-c][1,4] Benzodiazepine Dimers," Bioorg. Med. Chem. 12(16):4337-4350, Aug. 15. 2004.
A. Kamal et al., "Synthesis of New Benzimidazole Linked Pyrrolo[2,1-c][1,4] Benzodiazepine Conjugates with Efficient DNA-Binding Affinity and Potent Cytotoxicity," Bioorg. Med. Chem. Lett. 18(8):2594-2598, Web Release Mar. 16, 2008.
D. J. Kaplan et al., "Anthramycin Binding to Deoxyribonucleic Acid-Mytomycin C Complexes. Evidence for Drug-Induced Deoxyribonucleic Acid Conformational Change and Coo perativity in Mitomycin C Binding," Biochemistry 20(26):7572 Dec. 1981.
K. W. Kohn et al., "Reaction of Anthramycin with Deoxyribonuceic Acid," J. Mol. Biol. 51(3):551-572, 1970.
S. Kunimoto et al., "Mazethramycin, A New Member of Anthramycin Group Antibiotics," J. Antibiot. 33(6):665-667, Jun. 1980.
J. W. Lown et al., "Molecular Mechanism of Binding of Pyrrolo(1,4)benzodiazepine Antitumour Agents to Deoxyribonucleic Acid: Anthramycin and Tomaymycin," Biochem. Pharmacol. 28(13 :2017-2026, Jul. 1 1979.
M. A. Marques et al., "Expanding the Repertoire of Heterocycle Ring Pairs for Programmable Minor Groove DNA Recognition," J. Am. Chem. Soc. 126(33):10339-10349, Web Release Jul. 28, 2004.
P. Molina et al., "Synthesis of Pyrrolo[2, 1-c][1,4] benzodiazepines via an Intramolecular Aza-Wittig Reaction. Synthesis of the Antibiotic DC-81," Tetrahedron 51(19):5617-5630, May 8, 1995.
B. Nare et al., "Benzimidazoles, Potent Anti-Mitotic Drugs: Substrates for the P-Glycoprotein Transporter in Multidrug-Resistant Cells," Biochem. Pharmacol. 48(12):2215-2222, Dec. 16, 1994.
M. S. Newman, "Carcinogenic Activity of Benz[α] anthracenes," Carcinogenesis 1:203-207, 1976.
B. Z. Olenyuk et al., "Inhibition of Vascular Endothilial Growth Factor with a Sequence-Specific Hypoxia Response Element Antagonist," Proc. Natl. Acad. Sci. USA 101(48):16768-16773, Nov. 30, 2004.
M. Pedini et al., "New Heterocyclic Derivatives of Benzimidazole with Germicidal Activity. Part XIII. In Vitro Aromatase Inhibitory Activity; Preliminary Observations," IL Farmaco 54:327-330, 1999.
K.-I. Schimizu et al., "Prothracarcin, A Novel Antitumor Antibiotic," J. Antibiot. 35(8):972-978, Aug. 1982.
D. E. Thurston et al., "The Molecular Recognition of DNA," Chem. Br. 26:767-772, 1990.
D. E. Thurston et al., "Synthesis of DNA-Interactive Pyrrolo[2,1-c][1,4]benzodiazepines," Chem. Rev. 94(2):433-465, Mar. 1994.
D. E. Thurston et al., "Synthesis of Sequence-Selective C8-Linked Pyrrolo[2,1-*c*][1,4]benzodiazepine DNA Interstrand Cross-Linking Agents," J. Org. Chem. 61(23):8141-8147, Web Release Nov. 15, 1996.
D. E. Thurston et al. (1990) "O-Debenzylation of a Pyrrolo[2,1-c][1,4]benzodiazepine in the Presence of a Carbinolamine Functionality: Synthesis of DC-81," Synthesis 81-84. Jan. 1990.
A. Viger et al., "Exploring the Limits of Benzimidazole DNA-Binding Oligomers for the Hypoxia Inducible Factor (HIF)," Bioorg. Med. Chem. 14(24):8539-8549, Dec. 15, 2006.
Yadagirl, B. et al. "Convenient Routes to Substitutes Benzimidazoles and Imidazolo[4,5-b]pyridines Using Nitrobenzene as Oxidant," Synthetic Commun. 20:955-963, 1990.

BENZIMIDAZOLE LINKED PYRROLO[2,1-C][1,4] BENZODIAZEPINE HYBRIDS AS POTENTIAL ANTITUMOUR AGENTS AND PROCESS FOR THE PREPARATION THEREOF

CROSS-REFERENCE TO RELATED APPLICATIONS

This application is the U.S. National Stage of International Application No. PCT/IN2008/000718, filed Oct. 31, 2008, which claims the benefit of Indian Patent Application 603/DEL/2008, filed Mar. 11, 2008, both of which are hereby incorporated by reference to the extent not inconsistent with the disclosure herewith.

FIELD OF THE INVENTION

The present invention relates to novel benzimidazole linked pyrrolo[2,1-c][1,4]benzodiazepine hybrids as potential antitumour agents. The present invention also relates to a process for the preparation of novel benzimidazole linked pyrrolo[2,1-c][1,4]benzodiazepine hybrids. Particularly, the present invention relates to benzimidazole linked pyrrolo[2,1-c][1,4]benzodiazepine hybrids of general formula A.

Formula A

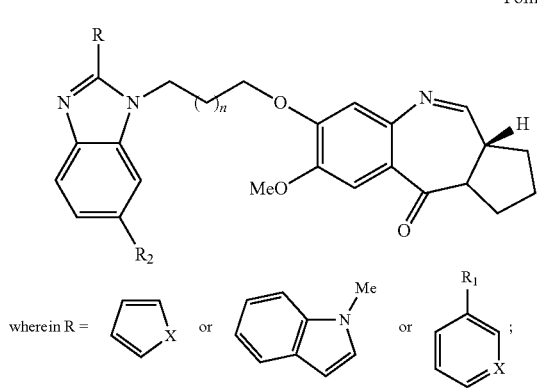

wherein R = furan, N-methylindole, or substituted phenyl x = O, S, NMe, C or N
R1 = H or OBn; R2 = H, COOEt or morpholine; n = 1-3

More particularly, the present invention relates to benzimidazole linked pyrrolo[2,1-c][1,4]benzodiazepine hybrids of general formula 8, 11 and 14 formula 8

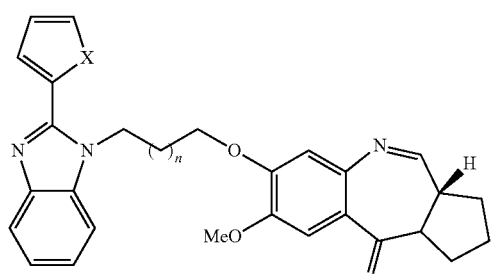

X = O, S, NMe    n = 1, 2, 3 formula 11

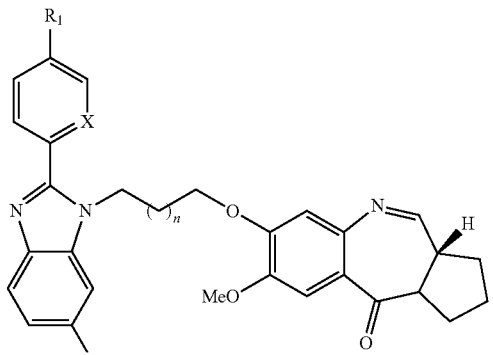

X = C, N
R1 = H, OBn
R2 = H, COOEt, morpholine
n = 1, 2, 3 formula 14

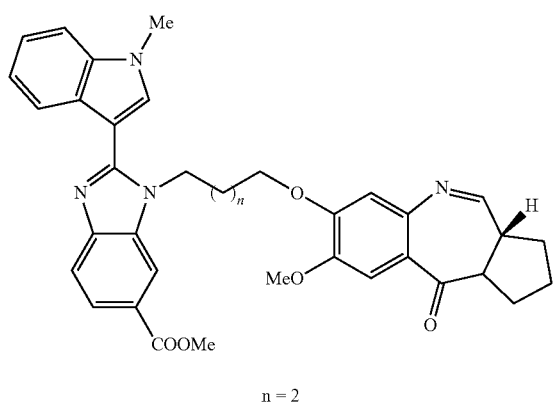

n = 2

The present invention further relates to a process for the preparation of 7-Methoxy-8-{n-[2-(2-furyl)-1H-benzimidazol-1-yl]alkyl}oxy-(11aS)-1,2,3,11a-tetrahydro-5H-pyrrolo[2,1-c][1,4]benzodiazepin-5-one/7-Methoxy-8-{n-[2-(2-thienyl)-1H-benzimidazol-1-yl]alkyl}oxy-(11aS)-1,2,3,11a-tetrahydro-5H-pyrr-olo[2,1-c][1,4]benzo diazepin-5-one/7-Methoxy-8-{n-[2-(1-Methyl-2-pyrrolyl)-1H-benzimidazol-1-yl]alkyl}oxy-(11aS)-1,2,3,11a-tetrahydro-5H-pyrrolo[2,1-c][1,4]benzodiazepin-5-one/7-Methoxy-8-{n-[2-(2-pyridyl)-1H-benzimidazol-1-yl]alkyl}oxy-(11aS)-1,2,3,11a-tetrahydro-5H-pyrrolo[2,1-c][1,4]benzodiazepin-5-one/Ethyl-2-[4-(benzyloxy)phenyl]-[(n-(11aS)-7-methoxy-1,2,3,11a-tetrahydro-5H-pyrrolo[2,1-c][1,4]benzodiazepin-5-one-8-yl)oxyalkyl]-2-benzi-midazol-6-carboxylate/7-Methoxy-8-{n-[2-[(4-(benzyloxy)phenyl)-6-morpholino]benzimidazol-1-yl]alkyl}oxy-(11aS)-1,2,3,11a-tetrahydro-5H-pyrrolo[2,1-c][1,4]benzodiazepin-5-one/Ethyl-1-[(n-(11aS)-7-methoxy-1,2,3,11a-tetrahydro-5H-pyrrolo[2,1-c][1,4]benzodiazepin-5-one-8-yl)oxyalkyl]-2-(1-methyl-3-indolyl)benzimidazol-6-carboxylate with aliphatic chain length variations.

BACKGROUND OF THE INVENTION

Pyrrolo[2,1-c][1,4]benzodiazepines (PBDs), a group of potent naturally occurring antitumour antibiotics from various *Streptomyces* species, are of considerable interest because of their ability to recognize and subsequently form covalent bonds to specific base sequence of double strand DNA (Dervan, P. B. *Science* 1989, 232, 464; Hurley, L. H. *J.*

Med. Chem. 1989, 32, 2027; Thurston, D. E.; Thompson, A. S. Chem. Br. 1990, 26, 767). Well-known members of this group include anthramycin, DC-81, sibiromycin, tomamycin, chicamycin and neothramycin of A and B (Hurley, L. H. J. Antibiot. 1977, 30, 349; Schimizu, K.; Kawamoto, I.; Tomita, F.; Morimoto, M.; Fujimoto, K. J. Antibiot. 1982, 35, 992; Lown, J. W.; Joshua, A. V. Biochem. Pharmacol. 1979, 28, 2017; Thurston, D. E.; Bose, D. S. Chem. Rev. 1994, 94, 433; Molina, P.; Diaz, I.; Tarraga, A. Tetrahedron 1995, 51, 5617; Kamal, A.; Rao, N. V. Chem. Commun. 1996, 385; Kamal, A.; Reddy, B. S. P.; Reddy, B. S, N. Tetrahedron Lett. 1996, 37, 6803). The cytotoxicity and antitumour activity of these agents are attributed to their property of sequence selective covalent binding to the N2 of guanine in the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; Unezawa, H. J. Antibiot., 1980, 33, 665; Kohn, K. W. and Speous, C. L. J. Mol. Biol., 1970, 51, 551; Hurley, L. H.; Gairpla, C. and Zmijewski, M. Biochem. Biophys. Acta., 1977, 475, 521; Kaplan, D. J. and Hurley, L. H. Biochemistry, 1981, 20, 7572). The molecules have a right-handed twist, which allows them to follow the curvature of the minor groove of B-form double-stranded DNA spanning three base pairs.

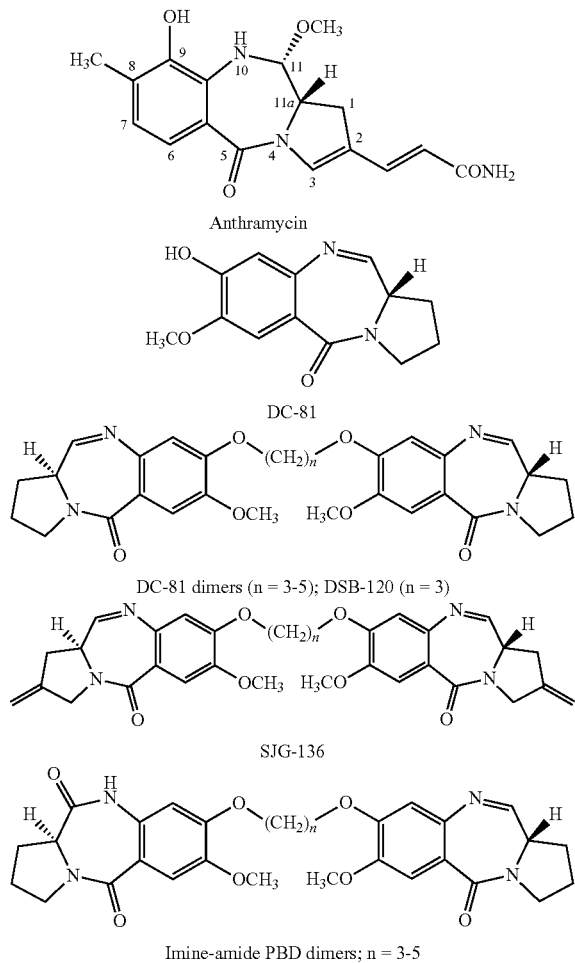

A recent development has been the linking of two PBD units through their C-8 positions to give bisfunctional-alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S, and Hurley, L. H. J. Org. Chem. 1996, 61, 8141).

Recently, PBD dimers have been developed that comprise of two C2-exo-methylene substituted DC-81 subunits tethered through their C-8 position via an inert propanedioxy linker (Gregson, S. J.; Howard, P. W.; Hartely, J. A.; Brooks, N. A.; Adams, L. J.; Jenkins, T. C.; Kelland, L. R. and Thurston, D. E. J. Med. Chem. 2001, 44, 737). A non-cross-linking mixed imine-amide PBD dimers have been synthesized that have significant DNA binding ability and potent antitumour activity (Kamal, A.; Ramesh, G. Laxman, N.; Ramulu, P.; Srinivas, O.; Neelima, K.; Kondapi, A. K.; Srinu, V. B.; Nagarajaram, H. M. J. Med. Chem. 2002, 45, 4679). However, the clinical efficacy for these antibiotics is hindered by several limitations, such as poor water solubility, cardiotoxicity, development of drug resistance and metabolic inactivation. Due to the excellent activity of these molecules, there is need to develop novel derivatives which are devoid of above limitations.

Benzimidazoles are small synthetic molecules that contain a benzene ring fused to a imidazole ring. These simple molecules have shown remarkable antitumour properties, whose mode of action is thought to result from their inhibition of microtubule formations (Nare, B.; Liu, Z.; Prichard, R. K. and George, E. Biochem Pharmacol. 1994, 48, 2215). Substituted benzimidazoles have proven as drug leads, which have exhibited pharmacological interest (Al-Mahaimeed, H. Int. Med. Res. 1997, 25, 175). In addition 2-substituted benzimidazoles cover a broad range of biological activities, including antitumour (Pedini, M.; Bistocchi, G. A.; Meo, G. D.; Lepri, E.; Bastianini, L. Il Farmaco 1999, 54, 327; Hida, F.; Robert, J.; Duc, L. C. Farmaco 1994, 49, 489). A series of 2-aryl benzimidazole-4-carboxamides have been synthesized and evaluated for in vitro and in vivo antitumour activity and DNA binding affinity (Denny, W. A.; Rewcastle, G. W. and Baguly, B. C. J. Med. Chem. 1990, 33, 814). Moreover, the architecture of benzimidazole moiety as a new platform for the DNA-minor groove recognition elements for (Marques, M. A.; Doss, R. M.; Foister, S.; Dervan, P. B. J. Am. Chem. Soc. 2004, 126, 10339), selective base pair recognition can be achieved by introduction of heteroatoms and substituents in this ring system (Viger, A.; Dervan, P. B. Bioorg. Med. Chem. 2006, 14, 8539; Foister, S.; Marques, M. A.; Doss, R. M.; Dervan, P. B. Bioorg. Med. Chem. 2003, 11, 4333). This ring system can also be considered as a new tool for the target specific transcription factor at the binding sites relevant to biological systems. Recently, Dervan and coworkers reported the down-regulation of the angiogenetic vascular endothelial growth factor (VEGF) by a DNA-binding fluorescein-polyamide conjugate in cell culture (Olenyuk, B. Z.; Zhang, G.; Klco, J. M.; Nickols, N. G.; Kaelin, W. G.; Jr.; Dervan, P. B. Proc. Natl. Acad. Sci. U.S.A. 2004, 101, 16768). Based on the potent anticancer activity of pyrrolo[2,1-c][1,4]benzodiazepines and benzimidazole ring system the new PBD hybrids have been designed and synthesized by linking benzimidazole moieties at C8-position of pyrrolo[2,1-c][1,4]benzodiaze-pine with varying alkane spacers.

OBJECTIVES OF THE INVENTION

The main objective of the present invention is to provide novel benzimidazole linked pyrrolo[2,1-c][1,4]benzodiazepine hybrids useful as antitumour agents.

Yet another object of the present invention is to provide a process for the preparation of novel benzimidazole linked pyrrolo[2,1-c][1,4]benzodiazepine hybrids.

SUMMARY OF THE INVENTION

Accordingly the present invention provides novel pyrrolo[2,1-c][1,4]benzodiazepine hybrids of general formula A,

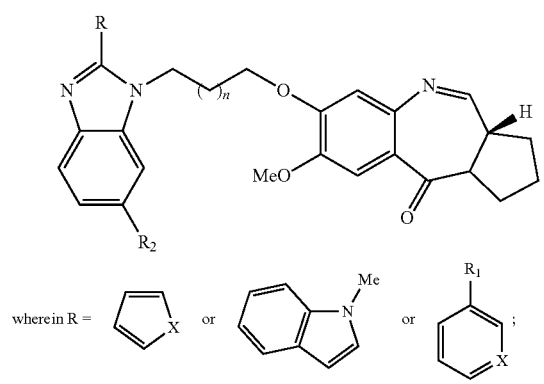

wherein R = [structures shown] or [structures shown] or [structures shown];

x = O, S, NMe, C or N
R1 = H or OBn; R2 = H, COOEt or morpholine; n = 1-3

In an embodiment of the present invention the novel pyrrolo[2,1-c][1,4]benzodiazepine hybrids of general formula A according to claim 1 is represented by the group of the following compounds a) 7-Methoxy-8-{3-[2-(2-furyl)-1H-benzimidazol-1-yl]propyl}oxy-(11aS)-1,2,3,11a-tetrahydro-5H-pyrrolo[2,1-c][1,4]benzodiazepin-5-one (8a);

b) 7-Methoxy-8-{4-[2-(2-furyl)-1H-benzimidazol-1-yl]butyl}oxy-(11aS)-1,2,3,11a-tetrahydro-5H-pyrrolo[2,1-c][1,4]benzodiazepin-5-one (8b);

c) 7-Methoxy-8-{5-[2-(2-furyl)-1H-benzimidazol-1-yl]pentyl}oxy-(11aS)-1,2,3,11a-tetrahydro-5H-pyrrolo[2,1-c][1,4]benzodiazepin-5-one (8c);

d) 7-Methoxy-8-{3-[2-(2-thienyl)-1H-benzimidazol-1-yl]propyl}oxy-(11aS)-1,2,3,11a-tetrahydro-5H-pyrrolo[2,1-c][1,4]benzodiazepin-5-one (8d);

e) 7-Methoxy-8-{4-[2-(2-thienyl)-1H-benzimidazol-1-yl]butyl}oxy-(11aS)-1,2,3,11a-tetrahydro-5H-pyrrolo[2,1-c][1,4]benzodiazepin-5-one (8e);

f) 7-Methoxy-8-{5-[2-(2-thienyl)-1H-benzimidazol-1-yl]pentyl}oxy-(11aS)-1,2,3,11a-tetrahydro-5H-pyrrolo[2,1-c][1,4]benzodiazepin-5-one (8f);

g) 7-Methoxy-8-{3-[2-(1-Methyl-2-pyrrolyl)-1H-benzimidazol-1,4]propyl}-oxy-(11aS)-1,2,3,11a-tetrahydro-5H-pyrrolo[2,1-c][1,4]benzodiazepin-5-one (8g).

h) 7-Methoxy-8-{3-[2-(2-pyridyl)-1H-benzimidazol-1-yl]propyl}oxy-(11aS)-1,2,3,11a-tetrahydro-5H-pyrrolo[2,1-c][1,4]benzodiazepin-5-one (11a);

i) 7-Methoxy-8-{5-[2-(2-pyridyl)-1H-benzimidazol-1-yl]pentyl}oxy-(11aS)-1,2,3,11a-tetrahydro-5H-pyrrolo[2,1-c][1,4]benzodiazepin-5-one (11b);

j) 7-Methoxy-8-{5-[2-[(4-(benzyloxy)phenyl)-6-morpholino]benzimidazol-1-yl]pentyl}oxy-(11aS)-1,2,3,11a-tetrahydro-5H-pyrrolo[2,1-c][1,4]benzodiazepin-5-one (11c).

k) Ethyl-2-[4-(benzyloxy)phenyl]-[(5-(11aS)-7-methoxy-1,2,3,11a-tetrahydro-5H-pyrrolo[2,1-c][1,4]benzodiazepin-5-one-8-yl)oxypentyl]-2-benzimidazol-6-carboxylate (11d);

l) Methyl-1-[(4-(11aS)-7-methoxy-1,2,3,11a-tetrahydro-5H-pyrrolo[2,1-c][1,4]benzodiazepin-5-one-8-yl)oxybutyl]-2-(1-methyl-3-indolyl)benzimidazol-6-carboxylate (14).

In yet another embodiment the structural formula of the represented compounds of novel pyrrolo[2,1-c][1,4]benzodiazepine hybrids are

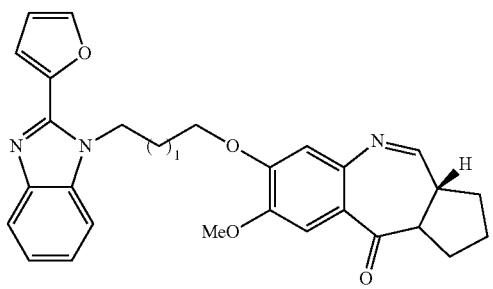

8a

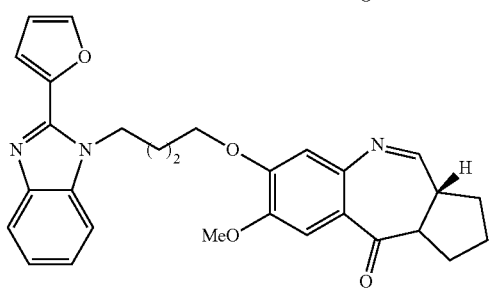

8b

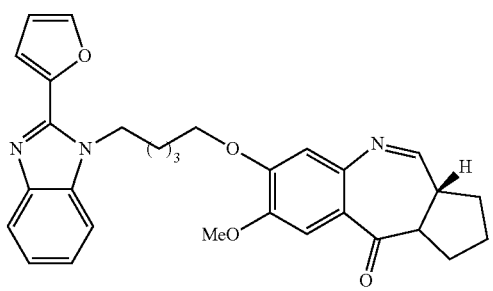

8c

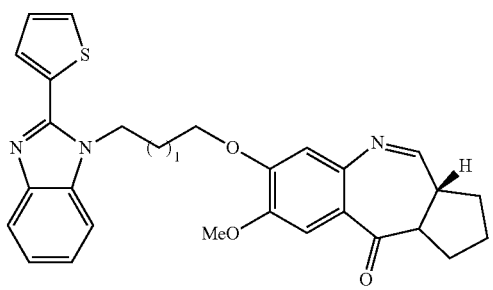

8d

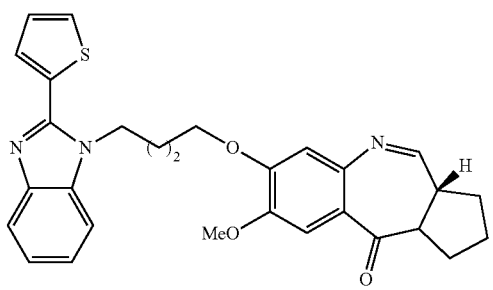

8e

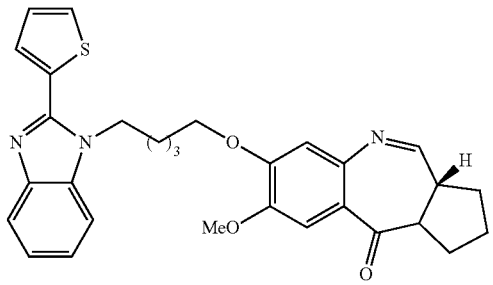

8f

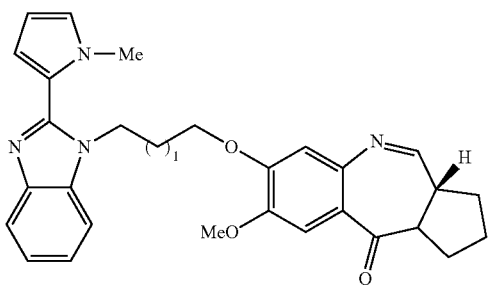

8g

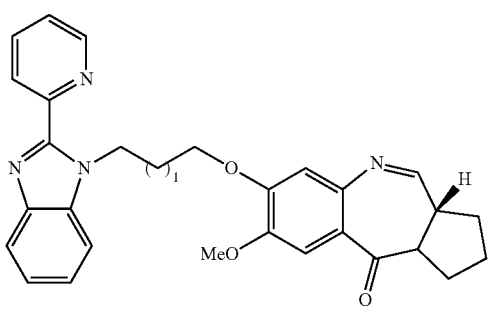

11a

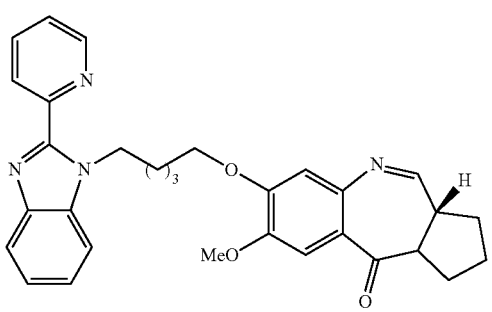

11b

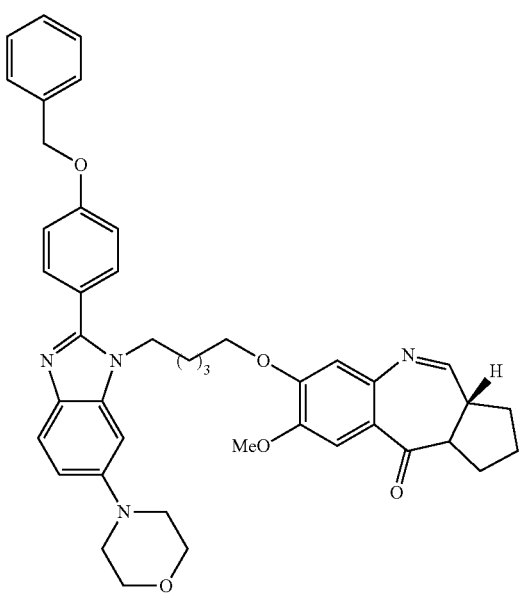

11c

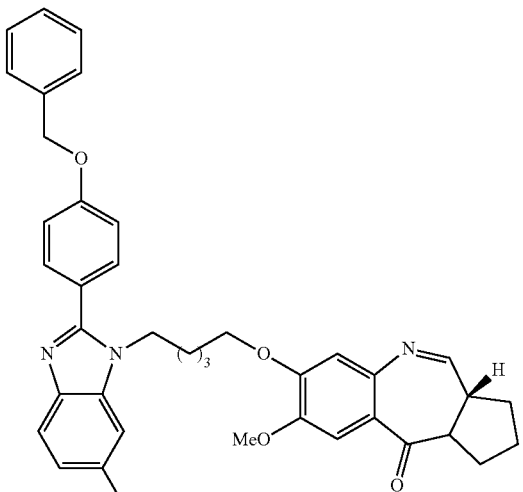

11d

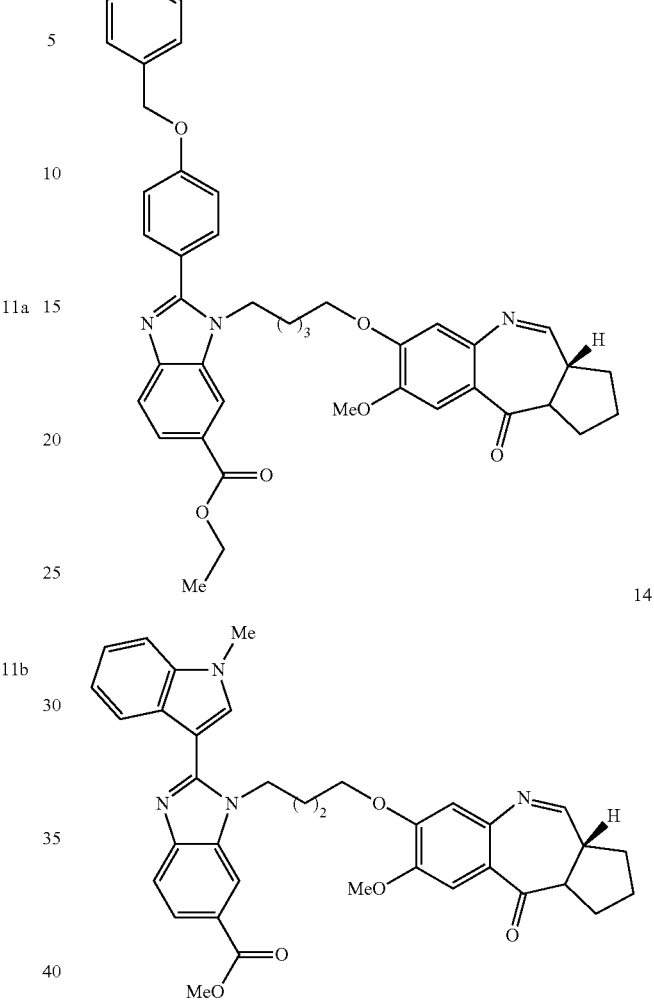

14

In yet another embodiment the novel pyrrolo[2,1-c][1,4] benzodiazepine hybrids exhibits of formula A an in vitro anticancer/antitumour activity against sixty human cancer cell lines derived from nine cancer types selected from the group consisting of leukemia, non-small-cell lung, colon, CNS, melanoma, ovarian, prostate, and breast cancer.

The present invention further provides a pharmaceutical composition comprising novel pyrrolo[2,1-c][1,4]benzodiazepine hybrids, its derivatives, analogues, salts or mixture thereof optionally with pharmaceutically acceptable carriers, adjuvants and additives.

In yet another embodiment the novel pyrrolo[2,1-c][1,4] benzodiazepine hybrids used in pharmaceutical composition is represented by a general formula A,

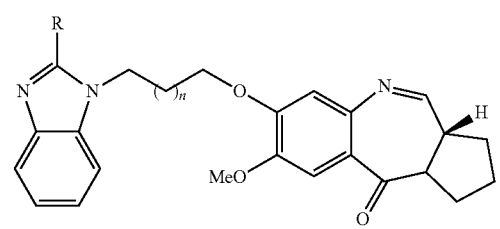

wherein R = 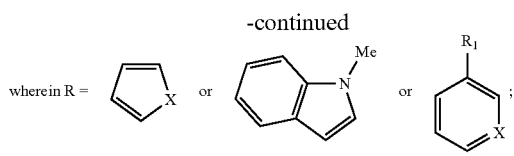

x = O, S, NMe, C or N;
R1 = H or OBn; R2 = H, COOEt or morpholine; n = 1-3

The present invention further provides a process for the preparation of benzimidazole linked pyrrolo[2,1-c][1,4]benzodiazine hybrids of general formula A

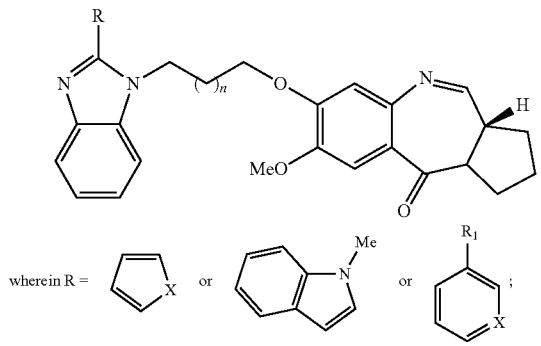

wherein R = x = O, S, NMe, C or N;
R1 = H or OBn; R2 = H, COOEt or morpholine; n = 1-3 and the said process comprising the steps of:
a) reacting (2S)—N-[4-(n-bromoalkyl)-oxy-5-methoxy-2-nitrobenzoyl]pyrrolidine-2-carboxaldehyde diethylthioacetal of formula 2a-c with benzimidazole derivatives of formula 3a-c, 4a-c or 5, isolating (2S)—N-{4-(n-[2-(2-furyl)benzimidazol-1-yl]alkyl)oxy-5-methoxy-2-nitrobenzoyl}pyrrolidine-2-carboxaldehyde diethyl thio acetal/(2S)—N-{4-(n-[2-(2-thienyl)benzimidazol-1-yl]alkyl)oxy-5-methoxy-2-nitro benzoyl}pyrrolidine-2-carboxaldehyde diethyl thioacetal/(2S)—N-{4-(n-[2-(1-methyl-2-pyrrolyl)benzimidazol-1-yl]alkyl)oxy-5-methoxy-2-nitrobenzoyl}pyrrolidine-2-carboxaldehyde diethyl thioacetal of formula 6a-g and (2S)—N-{4-(n-[2-(2-pyridyl)benzimidazol-1-yl]alkyl)oxy-5-methoxy-2-nitrobenoyl}pyrrolidine-2-carboxaldehyde diethyl thioacetal/(2S)—N-{4-(n-[2-[(4-(benzyloxy)phenyl)-6-morpholino]benzimidazol-1-yl]alkyl)oxy-5-methoxy-2-nitrobenzoyl}pyrrolidine-2-carboxaldehyde diethyl thioacetal/Ethyl-2-[4-(benzyloxy)phenyl]-{[n-[4-(2S)—N-pyrrolidine-2-carboxaldehydediethylthioacetal]alkyl]-2-methoxy-5-nitrophenoxy}benzimidazol-6-carboxylate of formula 0.9a-d and methyl-1-{[4-[4-(2S)—N-pyrrolidine-2-carboxaldehydediethylthioacetal]butyl]-2-methoxy-5-nitrophenoxy}-2-(1-methyl-3-indolyl)benzimidazol-6-carboxylate of formula 12, respectively:
b) reducing the above nitro compounds of formula 6a-g, 9a-d and 12 with SnCl$_2$.2H$_2$O, in presence of organic solvent selected from methanol and ethanol up to a reflux temperature, isolating the (2S)—N-{4-(n-[2-(2-furyl)benzimidazol-1-yl]alkyl)oxy-5-methoxy-2-aminobenzoyl}pyrrolidine-2-carboxaldehyde diethyl thio acetal/(2S)—N-{4-(n-[2-(2-thienyl)benzimidazol-1-yl]alkyl)oxy-5-methoxy-2-amino benzoyl}pyrrolidine-2-carboxaldehyde diethyl thioacetal/(2S)—N-{4-(n-[2-(1-methyl-2-pyrrolyl)benzimidazol-1-yl]alkyl)oxy-5-methoxy-2-aminobenzoyl}pyrrolidine-2-carboxaldehyde diethyl thioacetal of formula 7a-g, (2S)—N-{4-(n-[2-(2-pyridyl)benzimidazol-1-yl]alkyl)oxy-5-methoxy-2-aminobenoyl}pyrrolidine-2-carboxaldehyde diethyl thioacetal/(2S)—N-{4-(n-[2-[(4-(benzyloxy)phenyl)-6-morpholino]benzimidazol-1-yl]alkyl)-oxy-5-methoxy-2-aminobenzoyl}pyrrolidine-2-carboxaldehyde diethyl thioacetal/Ethyl-2-[4-(benzyloxy)phenyl]-{[n-[4-(2S)—N-pyrrolidine-2-carboxaldehyde diethyl thioacetal]alkyl]-2-methoxy-5-amino phenoxy}benzimidazol-6-carboxylate of formula 10a-d and methyl-1-{[4-[4-(2S)—N-pyrrolidine-2-carboxaldehyde diethylthioacetal]butyl]-2-methoxy-5-aminophenoxy}-2-(1-methyl-3-indolyl)benzimidazol-6-carboxylate of formula 13, respectively.
c) reacting the above amino compounds of formula 7a-g, 10a-d and 13 with mercurous chloride and calcium carbonate by known method to obtain the desired novel pyrrolo[2,1-c][1,4]benzodiazepine hybrids of formula 8a-g, 11a-d and 14.

DETAILED DESCRIPTION OF THE INVENTION

The precursors 2-(2-furyl)benzimidazole/2-(2-thienyl)benzimidazole/2-(1-methyl-2-pyrrolyl)benzimidazole of formula 3a-g (Brthini, Y.; Lown, J, W. *Synthetic Commun.* 1990, 20, 955; Hua, J. Y.; Bur, D.; Hasler, W.; Schmitt, V. R.; Dorn, A.; Bailly, C.; Waring, M. J.; Hochstrassera, R.; Leupina, W. *Bioorg. Med. Chem.* 2001, 9, 2905) and (2S)—N-[4-(hydroxy-5-methoxy-2-nitrobenzoyl]pyrrolidine-2-carboxaldehyde diethylthioacetal of formula 2 (Thurston, D. E.; Murthy, V. S.; Langley, D. R.; Jones, G. B. *Synthesis.* 1990, 81) have been prepared by literature methods. The other benzimidazole precursors 2-(2-pyridyl)benzimidazole/4-{2-[4-(Benzyloxy)phenyl]benzimidazol-6-yl}morpholine/Ethyl-2-[4-(benzyloxy)phenyl]benzimidazol-6-carboxilate of formula 4a-c have been prepared condensation followed by oxidation of substituted 2,3-diaminobenzene with benzylated protected benzaldehydes in presence of sodium metabisulphate (Kamal, A.; Ramulu, P.; Srinivas, O.; Ramesh, G.; Kumar, P, P. *Bioorg. Med. Chem. Lett.* 2004, 12, 4337). methyl-2-(1-methyl-3-indolyl)benzimidazol-6-carboxylate of formula 5 has been prepared by methyl 3,4-diaminobenzoate with corresponding 1-methyl-1H-3-indolecarbaldehyde These new analogues of pyrrolo[2,1-c][1,4]benzodiazepine hybrids linked at C-8 position have shown promising DNA binding activity and efficient anticancer activity in various cell lines. The molecules synthesized are of immense biological significance with potential sequence selective DNA-binding property. This present invention is illustrated in schemes 1-3 which comprise:
1) The ether linkage at C-8 position of DC-81 intermediates with benzimidazole moieties.
2) Refluxing the reaction mixtures for 48 h.
3) Synthesis of C-8 linked PBD antitumour antibiotic hybrid imines.
4) Purification by column chromatography using different solvents like ethyl acetate, hexane, chloroform and methanol.

Scheme 1

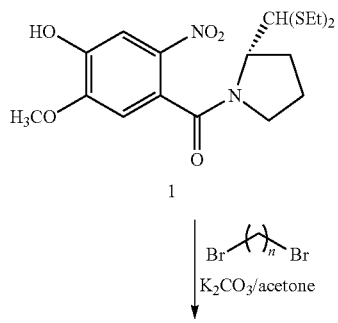

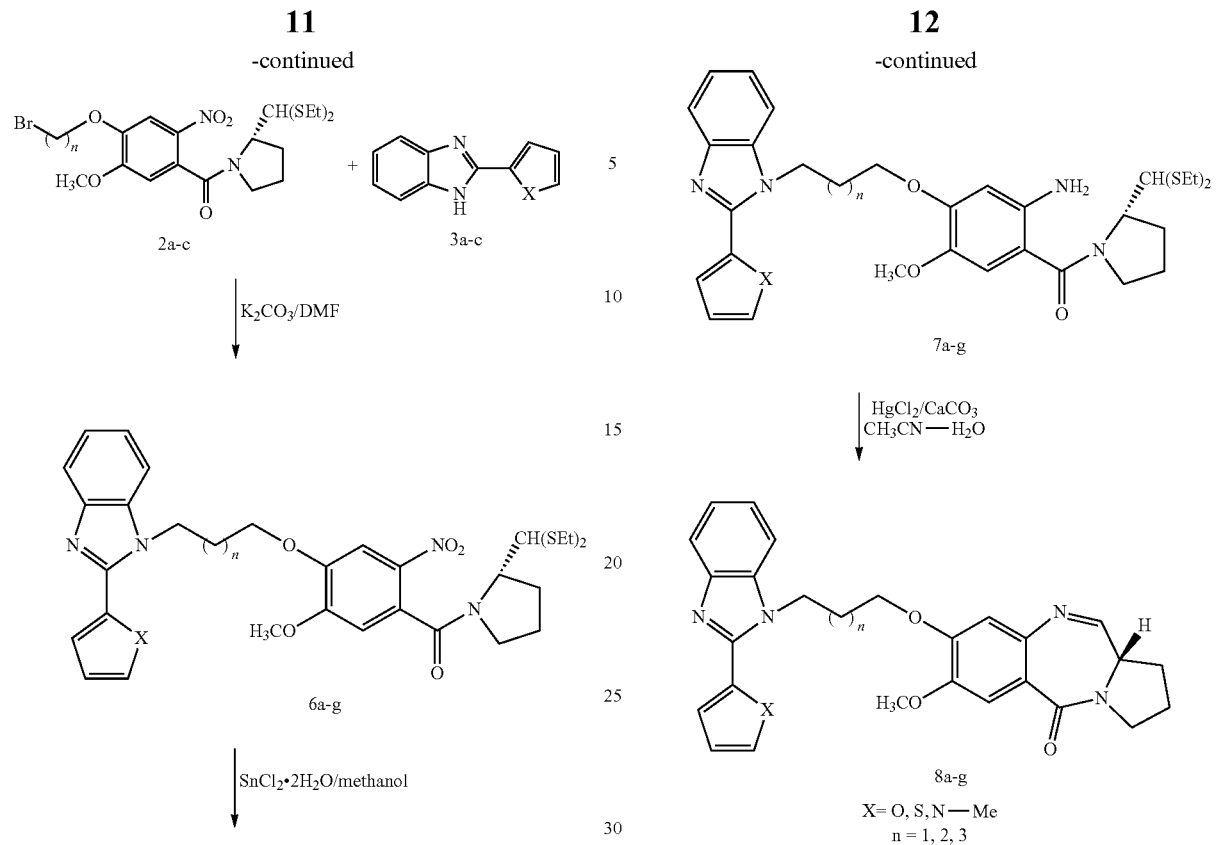
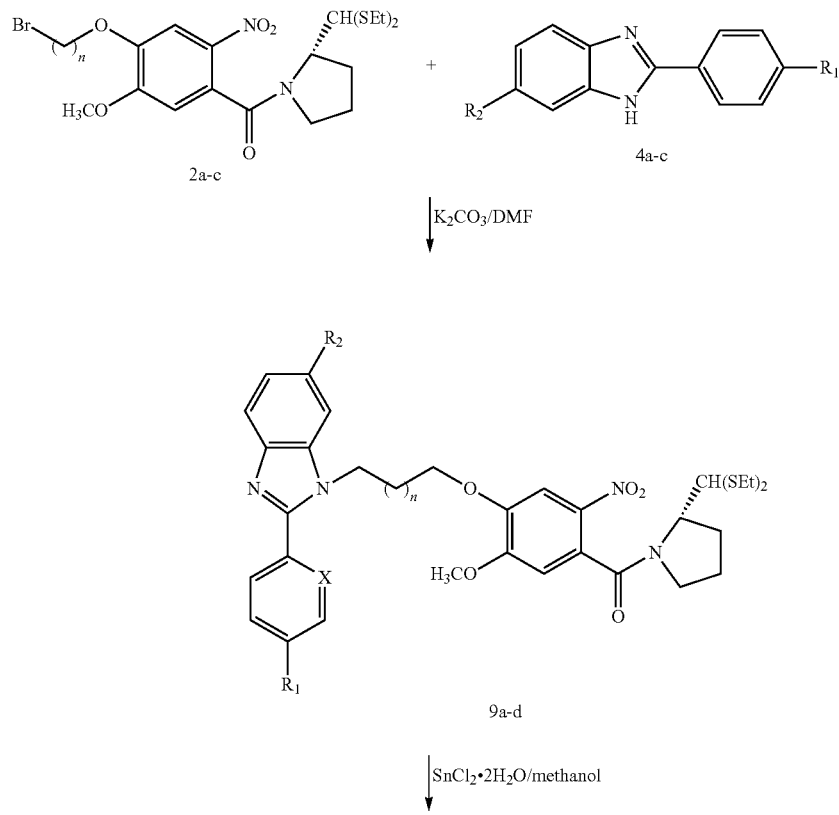

-continued
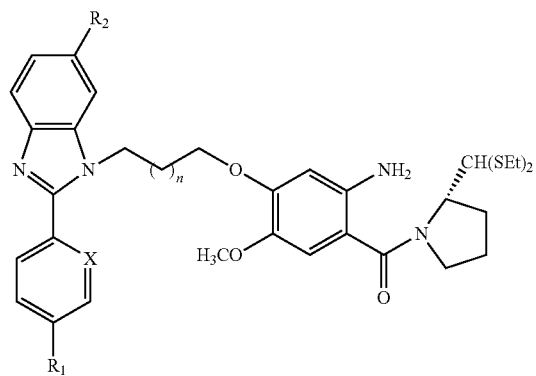
11a-d
↓ HgCl₂/CaCO₃
CH₃CN—H₂O
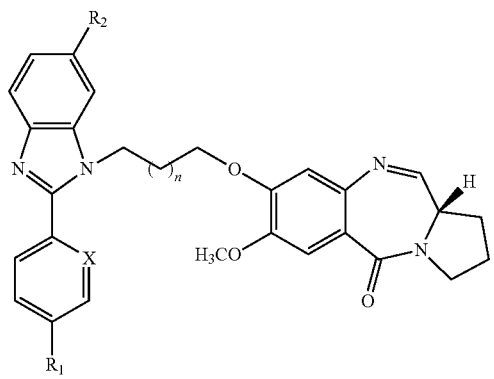
11a-d
X = C, N
R₁ = H, OBn
R₂ = H, COOEt, morpholine
n = 1, 3
Scheme 3
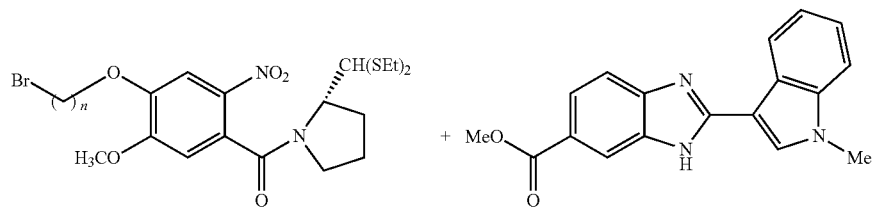
↓ K₂CO₃/DMF

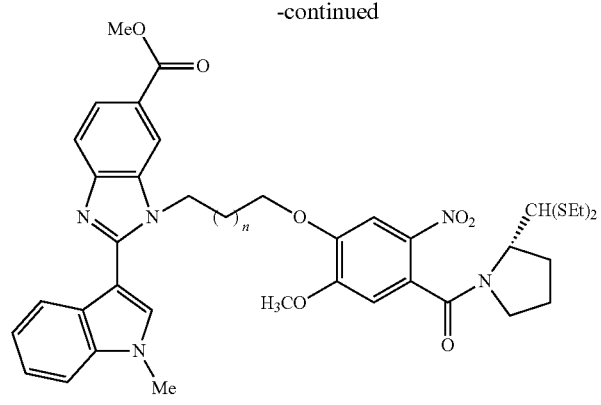
12
↓ SnCl₂·2H₂O/methanol
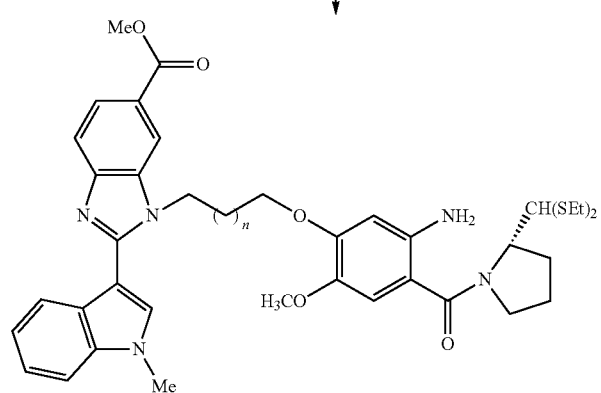
13
↓ HgCl₂/CaCO₃
CH₃CN—H₂O
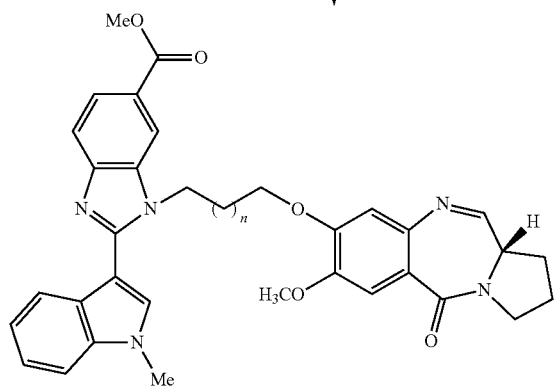
14
n = 2
Representative compounds 8a-g, 11a-d and 14 of general structural formula 8, 11 and 14
| Compound | n | X | R₁ | R₂ |
|---|---|---|---|---|
| 8a | 3 | O | — | — |
| 8b | 4 | O | — | — |
| 8c | 5 | O | — | — |
| 8d | 3 | S | — | — |
| 8e | 4 | S | — | — |
| 8f | 5 | S | — | — |

-continued

| Compound | n | X | R$_1$ | R$_2$ |
|---|---|---|---|---|
| 8g | 3 | NMe | — | — |
| 11a | 3 | N | H | H |
| 11b | 5 | N | H | H |
| 11c | 5 | C | OBn | Morpholine |
| 11d | 5 | C | OBn | COOEt |
| 14 | 4 | — | — | — |

The following examples are given by way of illustration of the working of the invention in actual practice and therefore should not be construed to limit the scope of present invention in any way.

Example 1

To a solution of (2S)—N-[4-(3-bromopropyl)oxy-5-methoxy-2-nitrobenzoyl)pyrrolidine-2-carboxarbaldehyde diethyl thioacetal 2a (521 mg, 1 mmol) in dry DMF (10 mL) was added anhydrous K$_2$CO$_3$ (552 mg, 4 mmol) and the 2-(2-furyl)benzimidazole 3a (185 mg, 1 mmol). The reaction mixture was stirred at room temperature for 48 h. TLC using ethyl acetate as a solvent system monitored the reaction. The potassium carbonate was removed by suction filtration and the solvent was removed under vacuum. The crude product was purified by column chromatography using 3% MeOH—CHCl$_3$ as eluent to afford pure compound of 6a (468 mg, 75%).

$^1$H NMR (CDCl$_3$): δ 8.63 (d, J=5.2 Hz, 1H), 8.44 (d, J=7.55, Hz, 1H), 7.78-7.88 (m, 2H), 7.46-7.53 (m, 2H), 7.23-7.35 (m, 2H), 6.80 (s, 1H), 5.07-5.18 (m, 2H), 4.8 (d, J=3.0, 1H), 4.65-4.72 (m, 1H), 4.07-4.15 (m, 2H), 3.99 (s, 3H), 3.16-3.32 (m, 2H), 2.69-2.90 (m, 4H), 2.50-2.62 (m, 2H), 2.26-2.35 (m, 2H), 1.34-1.42 (m, 6H).

ESIMS: m/z 625 (M$^+$).

The compound 6a (625 mg, 1 mmol) dissolved in methanol (20 mL) and added SnCl$_2$.2H$_2$O (1.125 g, 5 mmol) was refluxed for 5 h or until the TLC indicated that reaction was completed. The methanol was evaporated by vacuum and the aqueous layer was then carefully adjusted to pH 8 with 10% NaHCO$_3$ solution and then extracted with ethyl acetate and chloroform (2×30 ml and 2×30 mL). The combined organic phase was dried over Na$_2$SO$_4$ and evaporated under vacuum to afford the crude amino diethyl thioacetal 7a (487 mg, 80%), which was used directly in the next step.

A solution of 7a (609 mg, 1 mmol), HgCl$_2$ (613 mg, 2.26 mmol) and CaCO$_3$ (246 mg, 2.46 mmol) in acetonitrile-water (4:1) was stirred slowly at room temperature for overnight or until TLC indicates complete loss of starting material. The reaction mixture was diluted with ethyl acetate (30 ml) filtered through a celite. The clear redish organic supernatant was extracted with saturated 5% NaHCO$_3$ (20 ml), brine (20 ml) and the combined organic phase is dried (Na$_2$SO$_4$). The organic layer was evaporated in vacuum and purified by column chromatography (90% CH$_2$Cl$_2$-MeOH) to give compound 8a (264 mg, 56%). This material was repeatedly evaporated from CHCl$_3$ in vacuum to generate the imine form.

$^1$H NMR (CDCl$_3$): δ 7.82 (d, J=7.8 Hz, 1H), 7.67 (s, 2H), 7.55 (s, 1H), 7.42-7.52 (m, 3H), 7.07-7.19 (m, 2H), 6.72 (s, 1H), 5.06-5.18 (m, 1H), 4.58-4.76 (m, 2H), 4.05-4.15 (m, 1H), 4.00 (s, 3H), 3.78-3.90 (m, 1H), 3.65-3.75 (m, 1H), 3.45-3.65 (m, 1H), 2.38-2.49 (m, 1H), 2.25-2.36 (m, 1H), 1.95-2.15 (m, 4H).

ESIMS: m/z 471 (M$^+$+1).

Example 2

To a solution of (2S)—N-[4-(4-bromobutyl)oxy-5-methoxy-2-nitrobenzoyl)pyrrolidine-2-carboxarbaldehyde diethyl thioacetal 2b (535 mg, 1 mmol) in dry DMF (10 mL) was added anhydrous K$_2$CO$_3$ (552 mg, 4 mmol) and the 2-(2-furyl)benzimidazole 3a (185 mg, 1 mmol). The reaction mixture was stirred at room temperature for 48 h. TLC using ethyl acetate as a solvent system monitored the reaction. The potassium carbonate was removed by suction filtration and the solvent was removed under vacuum. The crude product was purified by column chromatography using 3% MeOH—CHCl$_3$ as eluent to afford pure compound of 6b (498 mg, 78%).

$^1$H NMR (CDCl$_3$): δ 7.71-7.75 (m, 1H), 7.58 (s, 1H), 7.54-7.57 (t, 1H), 7.34-7.39 (m, 1H), 7.21-7.26 (m, 3H), 6.77 (s, 1H), 6.58-6.59 (dd, J=1.8, J=3.3 Hz, 1H), 4.82 (d, J=3.7 Hz, 1H), 4.57-4.71 (m, 3H), 4.10 (t, J=5.4 Hz, 2H), 3.89 (s, 3H), 3.15-3.30 (m, 2H), 2.65-2.85 (m, 4H), 2.05-2.32 (m, 4H), 1.75-1.93 (m, 4H), 1.30-1.40 (m, 6H).

ESIMS: m/z 640 (M$^+$+1).

The compound 6b (639 mg, 1 mmol) dissolved in methanol (20 mL) and added SnCl$_2$.2H$_2$O (1.125 g, 5 mmol) was refluxed for 5 h or until the TLC indicated that reaction was completed. The methanol was evaporated by vacuum and the aqueous layer was then carefully adjusted to pH 8 with 10% NaHCO$_3$ solution and then extracted with ethyl acetate and chloroform (2×30 ml and 2×30 mL). The combined organic phase was dried over Na$_2$SO$_4$ and evaporated under vacuum to afford the crude amino diethyl thioacetal 7b (486 mg, 78%), which was used directly in the next step.

A solution of 7b (623 mg, 1 mmol), HgCl$_2$ (613 mg, 2.26 mmol) and CaCO$_3$ (246 mg, 2.46 mmol) in acetonitrile-water (4:1) was stirred slowly at room temperature for overnight or until TLC indicates complete loss of starting material. The reaction mixture was diluted with ethyl acetate (30 ml) filtered through a celite. The clear redish organic supernatant was extracted with saturated 5% NaHCO$_3$ (20 ml), brine (20 ml) and the combined organic phase is dried (Na$_2$SO$_4$). The organic layer was evaporated in vacuum and purified by column chromatography (92% CH$_2$Cl$_2$-MeOH) to give compound 8b (291 mg, 60%). This material was repeatedly evaporated from CHCl$_3$ in vacuum to generate the imine form.

$^1$H NMR (CDCl$_3$): δ 7.77 (d, J=7.5 Hz, 1H), 7.62-7.69 (d, J=3.7 Hz, 1H), 7.57 (s, 1H), 7.44-7.55 (m, 2H), 7.10-7.33 (m, 4H), 6.50 (s, 1H), 5.00-5.52 (m, 1H), 4.76 (t, J=5.0 Hz), 4.65 (t, J=6.7 Hz, 2H), 4.10-4.19 (m, 2H), 3.92 (s, 3H), 3.45-3.87 (m, 2H), 2.30-2.39 (m, 2H), 1.85-2.20 (m, 6H)

ESIMS: m/z 485 (M$^+$).

Example 3

To a solution of (2S)—N-[4-(5-bromopentyl)oxy-5-methoxy-2-nitrobenzoyl)pyrrolidine-2-carboxarbaldehyde diethyl thioacetal 2c (549 mg, 1 mmol) in dry DMF (10 mL) was added anhydrous K$_2$CO$_3$ (552 mg, 4 mmol) and the 2-(2-furyl)benzimidazole 3a (185 mg, 1 mmol). The reaction mixture was stirred at room temperature for 48 h. TLC using ethyl acetate as a solvent system monitored the reaction. The potassium carbonate was removed by suction filtration and the solvent was removed under vacuum. The crude product was purified by column chromatography using 3% MeOH—CHCl$_3$ as eluent to afford pure compound of 6c (470 mg, 72%).

$^1$H NMR (CDCl$_3$): δ 7.71-7.75 (m, 1H), 7.58 (s, 1H), 7.54-7.57 (m, 1H), 7.34-7.39 (m, 1H), 7.21-7.26 (m, 3H), 6.77 (s, 1H), 6.58-6.59 (dd, J=1.8, J=3.3 Hz, 1H), 4.82 (d, J=3.7 Hz, 1H), 4.57-4.71 (m, 3H), 4.10 (t, J=5.4 Hz, 2H), 3.89 (s, 3H), 3.18-3.28 (m, 1H), 2.95-3.05 (m, 1H), 2.65-2.90 (m, 4H), 2.40-2.55 (m, 2H), 1.56-2.40 (m, 3H), 1.32-1.44 (m, 6H)

ESIMS: m/z 654 (M$^+$).

The compound 6c (653 mg, 1 mmol) dissolved in methanol (20 mL) and added $SnCl_2.2H_2O$ (1.125 g, 5 mmol) was refluxed for 5 h or until the TLC indicated that reaction was completed. The methanol was evaporated by vacuum and the aqueous layer was then carefully adjusted to pH 8 with 10% $NaHCO_3$ solution and then extracted with ethyl acetate and chloroform (2×30 ml and 2×30 mL). The combined organic phase was dried over $Na_2SO_4$ and evaporated under vacuum to afford the crude amino diethyl thioacetal 7c (497 mg, 78%), which was used directly in the next step.

A solution of 7c (666 mg, 1 mmol), $HgCl_2$ (613 mg, 2.26 mmol) and $CaCO_3$ (246 mg, 2.46 mmol) in acetonitrile-water (4:1) was stirred slowly at room temperature for overnight. The reaction mixture was diluted with ethyl acetate (30 mL) filtered through a celite pad. The clear organic supernatant was extracted with saturated 5% $NaHCO_3$ (20 mL), brine (20 mL) and the combined organic phase was dried ($Na_2SO_4$). The organic layer was evaporated under vacuum and purified by column chromatography using $MeOH—CHCl_3$ (4%) to give compound 8c (323 mg, 60%). This material was repeatedly evaporated from $CHCl_3$ in vacuum to generate the imine form.

$^1H$ NMR ($CDCl_3$): δ 7.79 (d, J=7.5 Hz, 1H), 7.63-7.68 (d, J=3.7 Hz, 1H), 7.57 (s, 1H), 7.45-7.55 (m, 2H), 7.10-7.35 (m, 4H), 6.5 (s, 1H), 5.00-5.52 (m, 1H), 4.78 (t, J=5.0 Hz), 4.67 (t, J=6.7 Hz, 2H), 4.10-4.20 (m, 2H), 3.90 (s, 3H), 3.50-3.70 (m, 2H), 2.40-2.55 (m, 2H), 2.20-2.35 (m, 2H), 1.56-2.40 (m, 6H)

ESIMS: m/z 499 ($M^+$).

Example 4

To a solution of (2S)—N-[4-(3-bromopropyl)oxy-5-methoxy-2-nitrobenzoyl)pyrrolidine-2-carboxarbaldehyde diethyl thioacetal 2a (521 mg, 1 mmol) in dry DMF (10 mL) was added anhydrous $K_2CO_3$ (552 mg, 4 mmol) and the 2-(2-thienyl)benzimidazole 3b (201 mg, 1 mmol). The reaction mixture was stirred at room temperature for 48 h. TLC using ethyl acetate as a solvent system monitored the reaction. The potassium carbonate was removed by suction filtration and the solvent was removed under vacuum. The crude product was purified by column chromatography using 3% $MeOH—CHCl_3$ as eluent to afford pure compound of 6d (448 mg, 75%).

$^1H$ NMR ($CDCl_3$): δ 7.72-7.80 (dd, J=2.9, J=7.3 Hz, 1H), 7.63 (d, J=2.9 Hz, 1H), 7.51 (s, 1H), 7.46 (d, J=4.4 Hz, 1H), 7.34-7.42 (dd, J=2.2, J=5.8 Hz, 1H), 7.18-7.30 (m, 2H), 7.07-7.14 (dd, J=3.6, J=5.1 Hz, 1H), 6.8 (s, 1H), 4.80-4.86 (d, J=3.6 Hz, 1H), 4.62-4.76 (m, 3H), 4.08 (t, J=4.4 Hz, 2H), 3.98 (s, 3H), 3.10-3.40 (m, 2H), 2.60-2.90 (m, 4H), 2.20-2.55 (m, 2H), 2.20-2.34 (m, 2H), 1.70-2.15 (m, 2H), 1.45-1.65 (m, 2H), 1.30-1.45 (m, 6H).

ESIMS: m/z 641 ($M^+$).

The compound 6d (641 mg, 1 mmol) dissolved in methanol (20 mL) and added $SnCl_2.2H_2O$ (1.125 g, 5 mmol) was refluxed for 5 h or until the TLC indicated that reaction was completed. The methanol was evaporated by vacuum and the aqueous layer was then carefully adjusted to pH 8 with 10% $NaHCO_3$ solution and then extracted with ethyl acetate and chloroform (2×30 ml and 2×30 mL). The combined organic phase was dried over $Na_2SO_4$ and evaporated under vacuum to afford the crude amino diethyl thioacetal 7d (488 mg, 80%), which was used directly in the next step.

A solution of 7d (611 mg, 1 mmol), $HgCl_2$ (613 mg, 2.26 mmol) and $CaCO_3$ (246 mg, 2.46 mmol) in acetonitrile-water (4:1) was stirred slowly at room temperature for overnight or until TLC indicates complete loss of starting material. The reaction mixture was diluted with ethyl acetate (30 ml) filtered through a celite. The clear redish organic supernatant was extracted with saturated 5% $NaHCO_3$ (20 ml), brine (20 ml) and the combined organic phase is dried ($Na_2SO_4$). The organic layer was evaporated in vacuum and purified by column chromatography (96% $CH_2Cl_2$-MeOH) to give compound 8d (272 mg, 56%). This material was repeatedly evaporated from $CHCl_3$ in vacuum to generate the imine form.

$^1H$ NMR ($CDCl_3$): δ 7.77-7.84 (m, 1H), 7.67 (d, J=4.5 Hz, 1H), 7.56 (s, 1H), 7.48 (d, J=4.53 Hz, 1H), 7.45 (d, J=2.26 Hz, 1H), 7.23-7.36 (m, 1H), 7.11-7.16 (m, 2H), 6.71 (s, 1H), 5.08-5.12 (m, 1H), 4.69 (t, J=7.45 Hz, 2H), 4.04-4.18 (m, 1H), 3.99 (s, 3H), 3.78-3.92 (m, 1H), 3.50-3.75 (m, 2H), 2.25-2.50 (m, 4H), 2.00-2.15 (m, 2H).

ESIMS: m/z 487 ($M^+$+1).

Example 5

To a solution of (2S)—N14-(4-bromobutyl)oxy-5-methoxy-2-nitrobenzoyl)pyrrolidine-2-carboxarbaldehyde diethyl thioacetal 2b (535 mg, 1 mmol) in dry DMF (10 mL) was added anhydrous $K_2CO_3$ (552 mg, 4 mmol) and the 2-(2-thienyl)benzimidazole 3b (201 mg, 1 mmol). The reaction mixture was stirred at room temperature for 48 h. TLC using ethyl acetate as a solvent system monitored the reaction. The potassium carbonate was removed by suction filtration and the solvent was removed under vacuum. The crude product was purified by column chromatography using 5% $MeOH—CHCl_3$ as eluent to afford pure compound of 6e (484 mg, 74%).

$^1H$ NMR ($CDCl_3$): δ 7.75-7.82 (dd, J=3.9, J=7.0 Hz, 1H), 7.61 (s, 1H), 7.56-7.61 (m, 1H), 7.51 (d, J=6.2 Hz, 1H), 7.35-7.43 (m, 1H), 7.24-7.32 (m, 2H), 7.10-7.17 (m, 1H), 6.8 (s, 1H), 4.85 (d, J=3.12 Hz, 1H), 4.62-4.80 (m, 1H), 4.58 (t, J=7.0 Hz, 2H), 4.06-4.20 (m, 2H), 3.91 (s, 3H), 3.20-3.35 (m, 1H), 2.95-3.05 (m, 1H), 2.60-2.90 (m, 4H), 1.60-2.40 (m, 8H), 1.25-1.45 (m, 6H).

ESIMS: m/z 655 ($M^+$).

The compound 6e (655 mg, 1 mmol) dissolved in methanol (20 mL) and added $SnCl_2.2H_2O$ (1.125 g, 5 mmol) was refluxed for 5 h or until the TLC indicated that reaction was completed. The methanol was evaporated by vacuum and the aqueous layer was then carefully adjusted to pH 8 with 10% $NaHCO_3$ solution and then extracted with ethyl acetate and chloroform (2×30 ml and 2×30 mL). The combined organic phase was dried over $Na_2SO_4$ and evaporated under vacuum to afford the crude amino diethyl thioacetal 7e (512 mg, 82%), which was used directly in the next step.

A solution of 7e (625 mg, 1 mmol), $HgCl_2$ (613 mg, 2.26 mmol) and $CaCO_3$ (246 mg, 2.46 mmol) in acetonitrile-water (4:1) was stirred slowly at room temperature for overnight or until TLC indicates complete loss of starting material. The reaction mixture was diluted with ethyl acetate (30 ml) filtered through a celite. The clear redish organic supernatant was extracted with saturated 5% $NaHCO_3$ (20 ml), brine (20 ml) and the combined organic phase is dried ($Na_2SO_4$). The organic layer was evaporated in vacuum and purified by column chromatography (95% $CH_2Cl_2$-MeOH) to give compound 8e (300 mg, 60%). This material was repeatedly evaporated from $CHCl_3$ in vacuum to generate the imine form.

$^1H$ NMR ($CDCl_3$): δ 7.75-7.85 (m, 1H), 7.69 (d, J=4.5 Hz, 1H), 7.54 (s, 1H), 7.50 (d, J=4.5, 1H), 7.40-7.47 (m, 1H), 7.26-7.34 (m, 3H), 7.07-7.16 (dd, J=3.7, J=5.2 Hz, 1H), 6.80 (s, 1H), 4.94-5.04 (m, 1H), 4.53 (t, J=7.5 Hz, 2H), 4.00-4.25 (m, 2H), 3.92 (s, 3H), 3.45-3.89 (m, 2H), 2.30-2.40 (m, 2H), 1.85-2.19 (m, 6H)

ESIMS: m/z 501 ($M^+$).

Example 6

To a solution of (2S)—N-[4-(5-bromopentyl)oxy-5-methoxy-2-nitrobenzoyl)pyrrolidine-2-carboxarbaldehyde diethyl thioacetal 2c (549 mg, 1 mmol) in dry DMF (10 mL) was added anhydrous $K_2CO_3$ (552 mg, 4 mmol) and the 2-(2-thienyl)benzimidazole 3b (201 mg, 1 mmol). The reaction mixture was stirred at room temperature for 48 h. TLC using ethyl acetate as a solvent system monitored the reaction. The potassium carbonate was removed by suction filtration and the solvent was removed under vacuum. The crude product was purified by column chromatography using 3% MeOH—$CHCl_3$ as eluent to afford pure compound of 6f (501 mg, 75%).

$^1$H NMR ($CDCl_3$): δ 7.74-7.81 (dd, J=1.7, J=6.0 Hz, 1H), 7.63-7.67 (m, 1H), 7.53 (s, 1H), 7.47 (d, J=4.3 Hz, 1H), 7.34-7.43 (m, 1H), 7.20-7.30 (m, 2H), 7.09-7.18 (m, 1H), 6.8 (s, 1H), 4.85 (d, J=4.3 Hz, 1H), 4.64-4.76 (m, 3H), 4.05-4.15 (t, J=4.3 Hz, 2H), 4.00 (s, 3H), 3.18-3.28 (m, 1H), 2.95-3.05 (m, 1H), 2.65-2.90 (m, 4H), 2.40-2.55 (m, 2H), 2.20-2.35 (m, 2H), 1.56-2.40 (m, 6H), 1.32-1.44 (m, 6H)

ESIMS: m/z 669 ($M^+$+1).

The compound 6f (669 mg, 1 mmol) dissolved in methanol (20 mL) and added $SnCl_2.2H_2O$ (1.125 g, 5 mmol) was refluxed for 5 h or until the TLC indicated that reaction was completed. The methanol was evaporated by vacuum and the aqueous layer was then carefully adjusted to pH 8 with 10% $NaHCO_3$ solution and then extracted with ethyl acetate and chloroform (2×30 ml and 2×30 mL). The combined organic phase was dried over $Na_2SO_4$ and evaporated under vacuum to afford the crude amino diethyl thioacetal 7f (530 mg, 83%), which was used directly in the next step.

A solution of 7f (639 mg, 1 mmol), $HgCl_2$ (613 mg, 2.26 mmol) and $CaCO_3$ (246 mg, 2.46 mmol) in acetonitrile-water (4:1) was stirred slowly at room temperature for overnight or until TLC indicates complete loss of starting material. The reaction mixture was diluted with ethyl acetate (30 ml) filtered through a celite. The clear redish organic supernatant was extracted with saturated 5% $NaHCO_3$ (20 ml), brine (20 ml) and the combined organic phase is dried ($Na_2SO_4$). The organic layer was evaporated in vacuum and purified by column chromatography (94% $CH_2Cl_2$-MeOH) to give compound 8f (298 mg, 58%). This material was repeatedly evaporated from $CHCl_3$ in vacuum to generate the imine form.

$^1$H NMR ($CDCl_3$): δ 7.72-7.80 (dd, J=1.7, J=6.0 Hz, 1H), 7.62-7.65 (m, 1H), 7.52 (s, 1H), 7.45 (d, J=4.3 Hz, 1H), 7.32-7.41 (m, 1H), 7.20-7.30 (m, 2H), 7.08-7.18 (m, 1H), 6.6 (s, 1H), 4.84 (d, J=4.3 Hz, 1H), 4.64-4.76 (m, 3H), 4.05-4.15 (t, J=4.3 Hz, 2H), 4.00 (s, 3H), 3.50-3.70 (m, 2H), 2.40-2.55 (m, 2H), 2.20-2.35 (m, 2H), 1.56-2.40 (m, 6H)

ESIMS: m/z 516 ($M^+$+1).

Example 7

To a solution of (2S)—N-[4-(3-bromopropyl)oxy-5-methoxy-2-nitrobenzoyl)pyrrolidine-2-carboxarbaldehyde diethyl thioacetal 2a (521 mg, 1 mmol) in dry DMF (10 mL) was added anhydrous $K_2CO_3$ (552 mg, 4 mmol) and the 2-(1-methyl-2-pyrrolyl)benzimidazol 3c (197 mg, 1 mmol). The reaction mixture was stirred at room temperature for 48 h. TLC using ethyl acetate as a solvent system monitored the reaction. The potassium carbonate was removed by suction filtration and the solvent was removed under vacuum. The crude product was purified by column chromatography using 3% MeOH—$CHCl_3$ as eluent to afford pure compound of 6g (445 mg, 70%).

$^1$H NMR ($CDCl_3$): δ 7.77-7.81 (m, 1H), 7.63 (s, 1H), 7.37-7.42 (m, 1H), 7.26-7.31 (m, 1H), 6.83-6.85 (dd, J=1.70, J=2.55 Hz, 1H), 6.81 (s, 1H), 6.46-6.48 (dd, J=1.70, J=3.77 Hz, 1H), 6.23-6.26 (dd, J=3.77, J=2.5 Hz, 1H), 4.87 (d, J=3.77 Hz, 1H), 4.67-4.75 (m, 1H), 4.33 (t, J=7.44 Hz, 2H), 4.05 (t, J=6.54 Hz, 2H), 3.90 (s, 3H), 3.88 (s, 3H), 3.17-3.34 (m, 2H), 2.67-2.87 (m, 4H), 2.22-2.31 (m, 1H), 2.089-2.16 (m, 1H), 1.82-2.01 (m, 2H), 1.51-1.60 (m, 2H), 1.30-1.43 (m, 6H).

ESIMS: m/z 639 ($M^+$+1).

The compound 6g (638 mg, 1 mmol) dissolved in methanol (20 mL) and added $SnCl_2.2H_2O$ (1.125 g, 5 mmol) was refluxed for 5 h or until the TLC indicated that reaction was completed. The methanol was evaporated by vacuum and the aqueous layer was then carefully adjusted to pH 8 with 10% $NaHCO_3$ solution and then extracted with ethyl acetate and chloroform (2×30 ml and 2×30 mL). The combined organic phase was dried over $Na_2SO_4$ and evaporated under vacuum to afford the crude amino diethyl thioacetal 7g (486 mg, 80%), which was used directly in the next step.

A solution of 7g (608 mg, 1 mmol), $HgCl_2$ (613 mg, 2.26 mmol) and $CaCO_3$ (246 mg, 2.46 mmol) in acetonitrile-water (4:1) was stirred slowly at room temperature for overnight or until TLC indicates complete loss of starting material. The reaction mixture was diluted with ethyl acetate (30 ml) filtered through a celite. The clear redish organic supernatant was extracted with saturated 5% $NaHCO_3$ (20 ml), brine (20 ml) and the combined organic phase is dried ($Na_2SO_4$). The organic layer was evaporated in vacuum and purified by column chromatography (90% $CH_2Cl_2$-MeOH) to give compound 8g (278 mg, 56%). This material was repeatedly evaporated from $CHCl_3$ in vacuum to generate the imine form.

$^1$H NMR ($CDCl_3$): δ 7.70-7.85 (m, 1H), 7.64 (d, J=4.6 Hz, 1H), 7.47 (s, 1H), 7.10-7.42 (m, 3H), 6.78-6.83 (m, 1H), 6.75 (s, 1H), 6.38-6.44 (dd, J=1.5, J=3.9 Hz, 1H), 6.21 (t, J=3.1 Hz, 1H), 5.00-5.13 (m, 1H), 4.25 (t, J=7.0 Hz, 2H), 3.97 (t, J=6.25 Hz, 2H), 3.88 (s, 3H), 3.81 (s, 3H), 3.40-3.60 (m, 2H), 2.15-2.35 (m, 2H), 1.70-2.10 (m, 4H).

ESIMS: m/z 484 ($M^+$+1).

Example 8

To a solution of (2S)—N-[4-(3-bromopropyl)oxy-5-methoxy-2-nitrobenzoyl)pyrrolidine-2-carboxarbaldehyde diethyl thioacetal 2a (521 mg, 1 mmol) in dry DMF (10 mL) was added anhydrous $K_2CO_3$ (552 mg, 4 mmol) and the 2-(2-pyridyl)benzimidazole 4a (195 mg, 1 mmol). The reaction mixture was stirred at room temperature for 48 h. TLC using ethyl acetate as a solvent system monitored the reaction. The potassium carbonate was removed by suction filtration and the solvent was removed under vacuum. The crude product was purified by column chromatography using 3% MeOH—$CHCl_3$ as eluent to afford pure compound of 9a (464 mg, 73%).

$^1$H NMR ($CDCl_3$): δ 8.65 (d, J=5.1 Hz, 1H), 8.45 (d, J=8.0 Hz, 1H), 7.75-7.88 (m, 2H), 7.47-7.52 (m, 1H), 7.46 (s, 1H), 7.20-7.36 (m, 3H), 6.78 (s, 1H), 4.86 (d, J=3.7 Hz, 1H), 4.54-4.70 (m, 3H), 4.00-4.14 (m, 2H), 3.98 (s, 3H), 3.18-3.28 (m, 1H), 2.94-3.04 (m, 1H), 2.64-2.90 (m, 4H), 2.40-2.55 (m, 2H), 1.55-2.40 (m, 4H), 1.30-1.44 (m, 6H)

ESIMS: m/z 636 ($M^+$).

The compound 9a (649 mg, 1 mmol) dissolved in methanol (20 mL) and added $SnCl_2.2H_2O$ (1.125 g, 5 mmol) was refluxed for 5 h or until the TLC indicated that reaction was completed. The methanol was evaporated by vacuum and the aqueous layer was then carefully adjusted to pH 8 with 10%

NaHCO$_3$ solution and then extracted with ethyl acetate and chloroform (2×30 ml and 2×30 mL). The combined organic phase was dried over Na$_2$SO$_4$ and evaporated under vacuum to afford the crude amino diethyl thioacetal 10a (485 mg, 80%), which was used directly in the next step.

A solution of 10a (606 mg, 1 mmol), HgCl$_2$ (613 mg, 2.26 mmol) and CaCO$_3$ (246 mg, 2.46 mmol) in acetonitrile-water (4:1) was stirred slowly at room temperature for overnight or until TLC indicates complete loss of starting material. The reaction mixture was diluted with ethyl acetate (30 ml) filtered through a celite. The clear redish organic supernatant was extracted with saturated 5% NaHCO$_3$ (20 ml), brine (20 ml) and the combined organic phase is dried (Na$_2$SO$_4$). The organic layer was evaporated in vacuum and purified by column chromatography (90% CH$_2$Cl$_2$-MeOH) to give compound 11a (250 mg, 52%). This material was repeatedly evaporated from CHCl$_3$ in vacuum to generate the imine form.

$^1$H NMR (CDCl$_3$): δ 8.68 (d, J=5.0 Hz, 1H), 8.48 (m, 1H), 7.65-7.69 (d, J=3.4 Hz, 1H), 7.75-7.88 (m, 2H), 7.49-7.52 (m, 1H), 7.47 (s, 1H), 7.22-7.36 (m, 3H), 6.79 (s, 1H), 5.04-5.19 (m, 1H), 4.52-4.76 (m, 2H), 4.04-4.14 (m, 1H), 4.02 (s, 3H), 3.77-3.90 (m, 1H), 3.67-3.75 (m, 1H), 3.46-3.65 (m, 1H), 2.39-2.50, (m, 1H), 2.26-2.36 (m, 1H), 1.94-2.15 (m, 4H).

ESIMS: m/z 483 (M$^+$+1).

Example 9

To a solution of (2S)—N-[4-(5-bromopentyl)oxy-5-methoxy-2-nitrobenzoyl)pyrrolidine-2-carboxarbaldehyde diethyl thioacetal 2c (549 mg, 1 mmol) in dry DMF (10 mL) was added anhydrous K$_2$CO$_3$ (552 mg, 4 mmol) and the 2-(2-pyridyl)benzimidazole 4a (195 mg, 1 mmol). The reaction mixture was stirred at room temperature for 48 h. TLC using ethyl acetate as a solvent system monitored the reaction. The potassium carbonate was removed by suction filtration and the solvent was removed under vacuum. The crude product was purified by column chromatography using 2% MeOH—CHCl$_3$ as eluent to afford pure compound of 9b (498 mg, 75%).

$^1$H NMR (CDCl$_3$): 8.62 (d, J=5.1 Hz, 1H), 8.44 (d, J=8.0 Hz, 1H), 7.75-7.87 (m, 2H), 7.47-7.51 (m, 1H), 7.45 (s, 1H), 7.20-7.35 (m, 3H), 6.77 (s, 1H), 4.82 (d, J=3.7 Hz, 1H), 4.57-4.71 (m, 3H), 4.02-4.15 (m, 2H), 3.97 (s, 3H), 3.10-3.30 (m, 1H), 2.90-3.08 (m, 1H), 2.65-2.85 (m, 4H), 2.45-2.62 (m, 2H), 1.60-2.40 (m, 6H), 1.44-1.50 (m, 2H), 1.30-1.42 (m, 6H)

ESIMS: m/z 666 (M$^+$).

The compound 9b (649 mg, 1 mmol) dissolved in methanol (20 mL) and added SnCl$_2$.2H$_2$O (1.125 g, 5 mmol) was refluxed for 5 h or until the TLC indicated that reaction was completed. The methanol was evaporated by vacuum and the aqueous layer was then carefully adjusted to pH 8 with 10% NaHCO$_3$ solution and then extracted with ethyl acetate and chloroform (2×30 ml and 2×30 mL). The combined organic phase was dried over Na$_2$SO$_4$ and evaporated under vacuum to afford the crude amino diethyl thioacetal 10b (519 mg, 82%), which was used in the directly next step.

A solution of 10b (634 mg, 1 mmol), HgCl$_2$ (613 mg, 2.26 mmol) and CaCO$_3$ (246 mg, 2.46 mmol) in acetonitrile-water (4:1) was stirred slowly at room temperature for overnight or until TLC indicates complete loss of starting material. The reaction mixture was diluted with ethyl acetate (30 ml) filtered through a celite. The clear redish organic supernatant was extracted with saturated 5% NaHCO$_3$ (20 ml), brine (20 ml) and the combined organic phase is dried (Na$_2$SO$_4$). The organic layer was evaporated in vacuum and purified by column chromatography (91% CH$_2$Cl$_2$-MeOH) to give compound 11b (285 mg, 56%). This material was repeatedly evaporated from CHCl$_3$ in vacuum to generate the imine form.

$^1$H NMR (CDCl$_3$): 8.69 (d, J=5.0 Hz, 1H), 8.43 (d, J=8.0 Hz, 1H), 7.74-7.86 (m, 2H), 7.46-7.50 (m, 1H), 7.45 (s, 1H), 7.20-7.37 (m, 3H), 6.78 (s, 1H), 5.02-5.52 (m, 1H), 4.76 (t, J=5.0 Hz), 4.66 (t, J=6.7 Hz, 2H), 4.10-4.20 (m, 2H), 3.92 (s, 3H), 3.52-3.70 (m, 2H), 2.42-2.55 (m, 2H), 2.22-2.35 (m, 2H), 1.56-2.40 (m, 6H)

ESIMS: m/z 510 (M$^+$).

Example 10

To a solution of (2S)—N-[4-(5-bromopentyl)oxy-5-methoxy-2-nitrobenzoyl)pyrrolidine-2-carboxarbaldehyde diethyl thioacetal 2c (52.1 mg, 1 mmol) in dry DMF (10 mL) was added anhydrous K$_2$CO$_3$ (552 mg, 4 mmol) and the 4-{2-[4-(Benzyloxy)phenyl]benzimidazol-6-yl}morpholine 4b (385 mg, 1 mmol). The reaction mixture was stirred at room temperature for 48 h. TLC using ethyl acetate as a solvent system monitored the reaction. The potassium carbonate was removed by suction filtration and the solvent was removed under vacuum. The crude product was purified by column chromatography using 5% MeOH—CHCl$_3$ as eluent to afford pure compound of 9c (602 mg, 73%).

$^1$H NMR (CDCl$_3$): δ 7.63 (d, J=9.0 Hz, 1H), 7.52-7.58 (m, 1H), 7.41-7.46 (m, 2H), 7.28-7.40 (m, 4H), 6.93 (d, J=9.0 Hz, 4H), 6.81 (s, 1H), 6.68 (s, 1H), 5.14 (s, 2H), 4.80 (d, J=3.7 Hz, 1H), 4.62-4.71 (m, 1H), 4.50-4.62 (m, 2H), 4.50-4.62 (m, 2H), 3.83-4.02 (m, 7H), 3.75-3.82 (m, 2H), 3.10-3.24 (m, 4H), 2.65-2.81 (m, 4H), 2.40-2.55 (m, 2H), 2.11-2.36 (m, 4H), 1.84-2.10 (m, 4H), 1.30-1.41 (m, 6H)

ESIMS: m/z 855 (M$^+$+1).

The compound 9c (826 mg, 1 mmol) dissolved in methanol (20 mL) and added SnCl$_2$.2H$_2$O (1.125 g, 5 mmol) was refluxed for 5 h or until the TLC indicated that reaction was completed. The methanol was evaporated by vacuum and the aqueous layer was then carefully adjusted to pH 8 with 10% NaHCO$_3$ solution and then extracted with ethyl acetate and chloroform (2×30 ml and 2×30 mL). The combined organic phase was dried over Na$_2$SO$_4$ and evaporated under vacuum to afford the crude amino diethyl thioacetal 10c (557 mg, 70%), which was used in the directly next step.

A solution of 10c (796 mg, 1 mmol), HgCl$_2$ (613 mg, 2.26 mmol) and CaCO$_3$ (246 mg, 2.46 mmol) in acetonitrile-water (4:1) was stirred slowly at room temperature for overnight or until TLC indicates complete loss of starting material. The reaction mixture was diluted with ethyl acetate (30 ml) filtered through a celite. The clear redish organic supernatant was extracted with saturated 5% NaHCO$_3$ (20 ml), brine (20 ml) and the combined organic phase is dried (Na$_2$SO$_4$). The organic layer was evaporated in vacuum and purified by column chromatography (90% CH$_2$Cl$_2$-MeOH) to give compound 11c (278 mg, 56%). This material was repeatedly evaporated from CHCl$_3$ in vacuum to generate the imine form.

$^1$H NMR (CDCl$_3$): δ 7.77 (s, 1H), 7.60-7.69 (d, J=3.6 Hz, 1H), 7.55-7.60 (m, 1H), 7.42-7.48 (m, 2H), 7.30-7.40 (m, 4H), 6.95 (d, J=9.0 Hz, 4H), 6.81 (s, 1H), 6.68 (s, 1H), 5.00-5.50 (m, 3H), 4.84 (d, J=4.3 Hz, 1H), 4.64-4.76 (m, 3H), 3.83-4.04 (m, 7H), 3.50-3.70 (m, 2H), 3.10-3.24 (m, 4H), 2.40-2.55 (m, 2H), 2.20-2.35 (m, 2H), 1.56-2.40 (m, 6H).

ESIMS: m/z 702 (M$^+$+1).

Example 11

To a solution of (2S)—N-[4-(5-bromopentyl)oxy-5-methoxy-2-nitrobenzoyl)pyrrolidine-2-carboxarbaldehyde diethyl thioacetal 2c (549 mg, 1 mmol) in dry DMF (10 mL) was added anhydrous $K_2CO_3$ (552 mg, 4 mmol) and the Ethyl-2-[4-(benzyloxy)phenyl]benzimidazol-6-carboxilate 4c (372 mg, 1 mmol). The reaction mixture was stirred at room temperature for 48 h. TLC using ethyl acetate as a solvent system monitored the reaction. The potassium carbonate was removed by suction filtration and the solvent was removed under vacuum. The crude product was purified by column chromatography using 5% MeOH—$CHCl_3$ as eluent to afford pure compound of 9d (588 mg, 70%).

$^1$H NMR ($CDCl_3$): δ 8.45 (s, 1H), 7.99-8.01 (dd, J=2.2, J=8.3 Hz, 1H), 7.60-7.68 (m, 3H), 7.55 (s, 1H), 7.29-7.44 (m, 5H), 7.07 (d, J=8.3 Hz, 2H), 6.57 (s, 1H), 5.13 (s, 2H), 4.82 (d, J=3.7 Hz, 1H), 4.62-4.70 (m, 1H), 4.36-4.46 (q, J=7.5 Hz, 2H), 4.25-4.35 (m, 2H), 3.85 (s, 3H), 3.84-3.29 (m, 2H), 2.65-2.85 (m, 4H), 2.17-2.32 (m, 0.2H), 1.85-2.11 (m, 6H), 1.44 (t, J=7.5 Hz, 3H), 1.29-1.39 (m, 6H)

ESIMS: m/z 830 ($M^+$+1).

The compound 9d (841 mg, 1 mmol) dissolved in methanol (20 mL) and added $SnCl_2.2H_2O$ (1.125 g, 5 mmol) was refluxed for 5 h or until the TLC indicated that reaction was completed. The methanol was evaporated by vacuum and the aqueous layer was then carefully adjusted to pH 8 with 10% $NaHCO_3$ solution and then extracted with ethyl acetate and chloroform (2×30 ml and 2×30 mL). The combined organic phase was dried over $Na_2SO_4$ and evaporated under vacuum to afford the crude amino diethyl thioacetal 10d (608 mg, 75%).

A solution of 10d (811 mg, 1 mmol), $HgCl_2$ (613 mg, 2.26 mmol) and $CaCO_3$ (246 mg, 2.46 mmol) in acetonitrile-water (4:1) was stirred slowly at room temperature for overnight or until TLC indicates complete loss of starting material. The reaction mixture was diluted with ethyl acetate (30 ml) filtered through a celite. The clear redish organic supernatant was extracted with saturated 5% $NaHCO_3$ (20 ml), brine (20 ml) and the combined organic phase is dried ($Na_2SO_4$). The organic layer was evaporated in vacuum and purified by column chromatography (90% $CH_2Cl_2$-MeOH) to give compound 11d (357 mg, 52%). This material was repeatedly evaporated from $CHCl_3$ in vacuum to generate the imine form.

$^1$H NMR ($CDCl_3$): δ 8.52 (s, 1H), 7.98-8.0 (m, 1H), 7.60-7.69 (m, 4H), 7.59 (s, 1H), 7.29-7.44 (m, 5H), 7.10 (d, J=8.3 Hz, 2H), 6.59 (s, 1H), 5.00-5.50 (m, 3H), 4.84 (d, J=4.3 Hz, 1H), 4.64-4.76 (m, 3H), 4.37-4.46 (q, J=7.5 Hz, 2H), 4.00-4.15 (m, 2H), 4.00 (s, 3H), 2.40-2.55 (m, 2H), 2.20-2.35 (m, 2H), 1.56-2.40 (m, 6H), 1.44 (t, J=7.5 Hz, 3H)

ESIMS: m/z 687 ($M^+$+1).

Example 12

To a solution of (2S)—N-[4-(4-bromobutyl)oxy-5-methoxy-2-nitrobenzoyl)pyrrolidine-2-carboxarbaldehyde diethyl thioacetal 2b (535 mg, 1 mmol) in dry DMF (10 mL) was added anhydrous $K_2CO_3$ (552 mg, 4 mmol) and the Ethyl 2-(1-methyl-3-indolyl)benzimidazol-6-carboxylate 5 (319 mg, 1 mmol). The reaction mixture was stirred at room temperature for 48 h. TLC using ethyl acetate as a solvent system monitored the reaction. The potassium carbonate was removed by suction filtration and the solvent was removed under vacuum. The crude product was purified by column chromatography using 2% MeOH—$CHCl_3$ as eluent to afford pure compound of 12 (472 mg, 60%).

$^1$H NMR ($CDCl_3$): δ 8.48 (s, 1H), 7.94-8.10 (m, 3H). 7.14-7.48 (m, 5H), 6.71 (s, 1H), 4.82 (d, J=3.5 Hz, 1H), 4.62-4.71 (m, 1H), 4.47-4.52 (m, 1H), 3.80 (s, 3H), 3.86 (t, J=5.2 Hz, 2H), 3.79 (s, 3H), 3.78 (s, 3H), 3.15-3.29 (m, 2H), 2.65-2.86. (m, 4H), 2.18-2.36 (m, 2H), 1.91-2.17 (m, 4H), 1.69-1.81 m, (m, 2H), 1.29-1.40 (m, 6H).

ESIMS: m/z 761 ($M^+$+1).

The compound 12 (774 mg, 1 mmol) dissolved in methanol (20 mL) and added $SnCl_2.2H_2O$ (1.125 g, 5 mmol) was refluxed for 5 h or until the TLC indicated that reaction was completed. The methanol was evaporated by vacuum and the aqueous layer was then carefully adjusted to pH 8 with 10% $NaHCO_3$ solution and then extracted with ethyl acetate and chloroform (2×30 ml and 2×30 mL). The combined organic phase was dried over $Na_2SO_4$ and evaporated under vacuum to afford the crude amino diethyl thioacetal 13 (490 mg, 80%), which was used in the directly next step.

A solution of 13 (758 mg, 1 mmol), $HgCl_2$ (788 mg, 2.26 mmol) and $CaCO_3$ (246 mg, 2.46 mmol) in acetonitrile-water (4:1) was stirred slowly at room temperature for overnight or until TLC indicates complete loss of starting material. The reaction mixture was diluted with ethyl acetate (30 ml) filtered through a celite. The clear redish organic supernatant was extracted with saturated 5% $NaHCO_3$ (20 ml), brine (20 ml) and the combined organic phase is dried ($Na_2SO_4$). The organic layer was evaporated in vacuum and purified by column chromatography (90% $CH_2Cl_2$-MeOH) to give compound 14 (341 mg, 55%). This material was repeatedly evaporated from $CHCl_3$ in vacuum to generate the imine form.

$^1$H NMR ($CDCl_3$): δ 8.49 (s, 1H), 7.99-8.12 (m, 3H), 7.60-7.69 (d, J=3.6 Hz, 1H), 7.14-7.48 (m, 5H), 6.71 (s, 1H), 5.00-5.50 (m, 1H), 4.76 (t, J=5.0 Hz, 2H), 4.65 (t, J=6.6 Hz, 2H), 4.36 (s, 3H), 3.92 (s, 3H), 3.81 (s, 3H), 3.45-3.87 (m, 2H), 2.30-2.39 (m, 2H), 1.85-2.20 (m, 6H)

ESIMS: m/z 606 ($M^+$+1).

Biological Activity:

DNA binding affinity of novel benzimidazole linked PBD hybrids (8a-g, 11a-d and 14):

Compounds have been subjected to thermal denaturation studies with duplex-form calf thymus DNA (CT-DNA) using an modification of a reported procedure (Newman, M. S. *Carcinog-compr. Surv.* 1976, 1, 203; (b) Hecht, S. S.; Loy, M.; Hoffman, *Carcinog-compr. Surv.* 1976, 1, 325). Working solutions in aqueous buffer (10 mM $NaH_2PO_4/Na_2HPO_4$, 1 mM $Na_2EDTA$, pH 7.00+0.01) containing CT-DNA (100 μm in phosphate) and the PBD (20 μm) have been prepared by addition of concentrated PBD solutions in DMSO to obtain a fixed [PBD]/[DNA] molar ratio of 1:5. The DNA-PBD solutions have been incubated at 37° C. for 0 and 18 h prior to analysis. Samples have been, monitored at 260 nm using a Beckman DU-800 spectrophotometer fitted with high performance temperature controller, and heated at 1° C. $min^{-1}$ in the 40-110° C. range. DNA helix→coil transition temperatures ($T_m$) have been obtained from the maxima in the d($A_{260}$)/d T derivative plots. Drug-induced alterations in DNA melting behavior are given by: $\Delta T_m=T_m(DNA+PBD)-T_m(DNA$ alone), where the $T_m$ value for the PBD-free CT-DNA is 69.1±0.01. The fixed [PBD]/[DNA] ratio used has not resulted in binding saturation of the host DNA duplex for any compound examined.

The DNA binding activity for these novel C8-linked benzimidazole-PBD hybrids has been examined by thermal denaturation studies using calf thymus (CT) DNA. Melting studies show that these compounds stabilize the thermal helix→coil or melting stabilization ($\Delta T_m$) for the CT-DNA duplex at pH 7.0, incubated at 37° C., where PBD/DNA molar ratio is 1:5. The data for the compounds 8a-g, 11a-d and 14 is included in Table 1 for comparison.

TABLE 1

Thermal denaturation data for benzimidazole linked PBD hybrids with calf thymus (CT) DNA

| PBD hybrids | [PBD]:[DNA] molar ratio[b] | ($\Delta T_m$ °C.)[a] after incubation at 37° C. for | |
|---|---|---|---|
| | | 0 h | 18 h |
| 8a | 1:5 | 5.1 | 6.1 |
| 8b | 1:5 | 0.1 | 1.0 |
| 8c | 1:5 | 5.1 | 7.0 |
| 8d | 1:5 | 3.9 | 5.1 |
| 8e | 1:5 | 0.1 | 1.0 |
| 8f | 1:5 | 6.1 | 6.1 |
| 8g | 1:5 | 2.0 | 3.1 |
| 11a | 1:5 | 3.0 | 4.2 |
| 11b | 1:5 | 1.0 | 1.2 |
| 11c | 1:5 | 2.9 | 3.2 |
| 11d | 1:5 | 2.0 | 3.0 |
| 14 | 1:5 | 1.5 | 2.0 |
| DC-81 | 1:5 | 0.3 | 0.7 |

[a] For CT-DNA alone at pH 7.00 ± 0.01, $T_m$ = 69.1° C. ± 0.01 (mean value from 10 separate determinations), all $\Delta T_m$ values are ±0.1-0.2° C.
[b] For a 1:5 molar ratio of [PBD]/[DNA], where CT-DNA concentration = 100 μM and ligand concentration = 20 μM in aqueous sodium phosphate buffer [10 mM sodium phosphate + 1 mM EDTA, pH 7.00 ± 0.01].

Anticancer activity: In vitro biological activity studies were carried out at the National Cancer Institute (USA).

The compounds were evaluated for in vitro anticancer activity against sixty human tumour cells derived from nine cancer types (leukemia, non-small-cell lung, colon, CNS, melanoma, ovarian, prostate, and breast cancer) as shown in Table 3. For each compound, dose response curves for each cell line were measured at a minimum of five concentrations at 10 fold dilutions. A protocol of 48 h continuous drug exposure was used and a sulforhodamine B (SRB) protein assay was used to estimate cell viability or growth. The concentration causing 50% cell growth inhibition (GI50), total cell growth inhibition (TGI 0% growth) and 50% cell death (LC50, −50% growth) compared with the control was calculated. The mean graph midpoint values of $\log_{10}$ TGI and $\log_{10}$ LC50 as well as $\log_{10}$ GI50 for 8c, 8e, 11a, 11c and 14 are listed in Table 2. As demonstrated by mean graph pattern, compound 8c exhibits an interesting profile of activity and selectivity for various cell lines. The mean graph mid point of $\log_{10}$ TGI and $\log_{10}$ LC50 showed similar pattern to the $\log_{10}$ GI50 mean graph mid points.

TABLE 2

$\log_{10}$GI50 $\log_{10}$TGI and $\log_{10}$LC50 mean graphs midpoints (MG_MID) of in vitro cytotoxicity data for the representative compounds against human tumour cell lines

| Compound | $\log_{10}$GI50 | $\log_{10}$TGI | $\log_{10}$LC50 |
|---|---|---|---|
| 8c | −7.91 | −6.89 | −4.60 |
| 8e | −5.81 | −5.18 | −4.51 |
| 11a | −5.75 | −5.14 | −4.42 |
| 11c | −5.83 | −5.00 | −4.24 |
| 14 | −6.19 | −5.65 | −4.92 |

TABLE 3

$\log_{10}$ GI50 (concentration in mol/L) values for the representative compounds 8a, 8e, 11a, 11c and 14

| Cancer | 8c | 8e | 11a | 11c | 14 |
|---|---|---|---|---|---|
| Leukemia | <−8.00 | −6.00 | −5.51 | −6.22 | −6.88 |
| Non-small-cell-lung | <−7.92 | −5.68 | −5.80 | −5.71 | −6.08 |

TABLE 3-continued $\log_{10}$ GI50 (concentration in mol/L) values for the representative compounds 8a, 8e, 11a, 11c and 14

| Cancer | 8c | 8e | 11a | 11c | 14 |
|---|---|---|---|---|---|
| Colon | <−7.92 | −5.71 | −5.72 | −5.64 | −6.04 |
| CNS | <−8.00 | −5.80 | −5.60 | −5.57 | −6.00 |
| Melanoma | <−7.92 | −5.80 | −5.66 | −5.81 | −6.27 |
| Ovarian | <−8.00 | −5.70 | −5.79 | −5.66 | −6.04 |
| Renal | <−7.92 | −5.80 | −5.85 | −6.12 | −6.10 |
| Prostate | <−7.64 | −5.88 | −5.87 | −5.66 | −6.62 |
| Breast | <−7.79 | −6.04 | −5.98 | −5.81 | −6.14 |

Each cancer type represents the average of six to nine different cancer cell lines.

We claim:
1. A compound of formula:

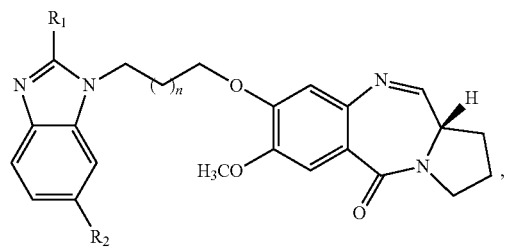

wherein $R_1$ =

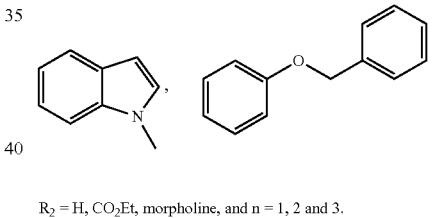

$R_2$ = H, $CO_2Et$, morpholine, and n = 1, 2 and 3.

2. A compound of claim 1 having one of the formulas:
a) 7-Methoxy-8-{3-[2-(2-furyl)-1H-benzimidazol-1-yl]propyl}oxy-(11aS)-1,2,3,11a-tetrahydro-5H-pyrrolo[2,1-c][1,4]benzodiazepin-5-one (8a);
b) 7-Methoxy-8-{4-[2-(2-furyl)-1H-benzimidazol-1-yl]butyl}oxy-(11aS)-1,2,3,11a-tetrahydro-5H-pyrrolo[2,1-c][1,4]benzodiazepin-5-one (8b);
c) 7-Methoxy-8-{5-[2-(2-furyl)-1H-benzimidazol-1-yl]pentyl}oxy-(11aS)-1,2,3,11a-tetrahydro-5/H-pyrrolo[2,1-c][1,4]benzodiazepin-5-one (8c);
d) 7-Methoxy-8-{3-[2-(2-thienyl)-1H-benzimidazol-1-yl]propyl}oxy-(11aS)-1,2,3,11a-tetrahydro-5H-pyrrolo[2,1-c][1,4]benzodiazepin-5-one (8d);
e) 7-Methoxy-8-{4-[2-(2-thienyl)-1H-benzimidazol-1-yl]butyl}oxy-(11aS)-1,2,3,11a-tetrahydro-5H-pyrrolo[2,1-c][1,4]benzodiazepin-5-one (8e);
f) 7-Methoxy-8-{5-[2-(2-thienyl)-1H-benzimidazol-1-yl]pentyl}oxy-(11aS)-1,2,3,11a-tetrahydro-5H-pyrrolo[2,1-c][1,4]benzodiazepin-5-one (8f);
g) 7-Methoxy-8-{3-[2-(1-Methyl-2-pyrrolyl)-1H-benzimidazol-1-yl]propyl}-oxy-(11aS)-1,2,3,11a-tetrahydro-5H-pyrrolo[2,1-c][1,4]benzodiazepin-5-one (8g);

h) 7-Methoxy-8-{3-[2-(2-pyridyl)-1H-benzimidazol-1-yl]propyl}oxy-(11aS)-1,2,3,11a-tetrahydro-5H-pyrrolo[2,1-c][1,4]benzodiazepin-5-one (11a);

i) 7-Methoxy-8-{5-[2-(2-pyridyl)-1H-benzimidazol-1-yl]pentyl}oxy-(11aS)-1,2,3,11a-tetrahydro-5H-pyrrolo[2,1-c][1,4]benzodiazepin-5-one (11b);

j) 7-Methoxy-8-{5-[2-[(4-(benzyloxy)phenyl)-6-morpholino]benzimidazol-1-yl]pentyl}oxy-(11aS)-1,2,3,11a-tetrahydro-5H-pyrrolo[2,1-c][1,4]benzodiazepin-5-one (11c); or k) Ethyl-2-[4-(benzyloxy)phenyl]-[(5-(11aS)-7-methoxy-1,2,3,11a-tetrahydro-5H-pyrrolo[2,1-c][1,4]benzodiazepin-5-one-8-yl)oxypentyl]-2-benzimidazol-6-carboxylate (11d).

3. A compound according to claim 1, wherein the structural formula of the represented compounds are 8a
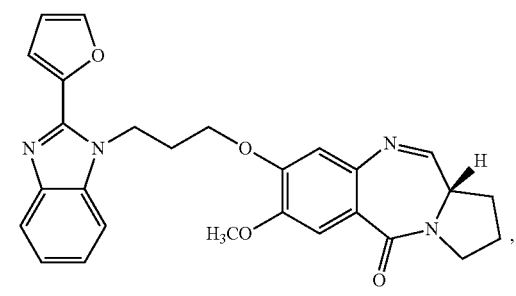

8b
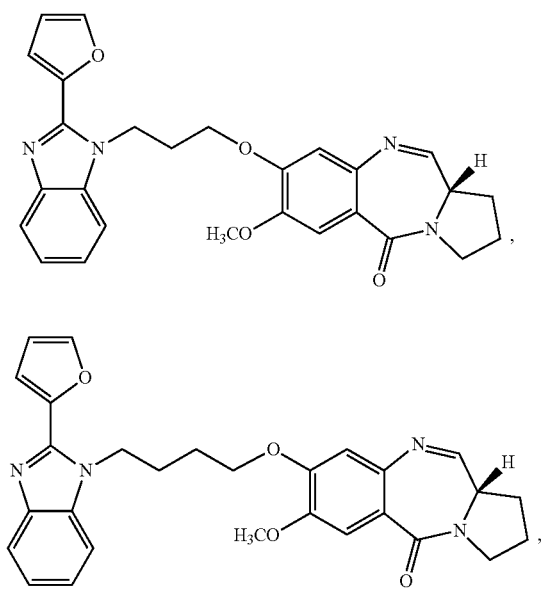

8c

8d
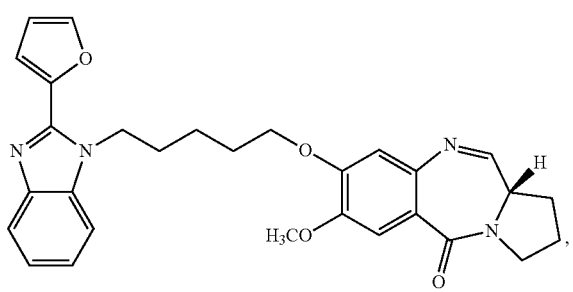

-continued

8e
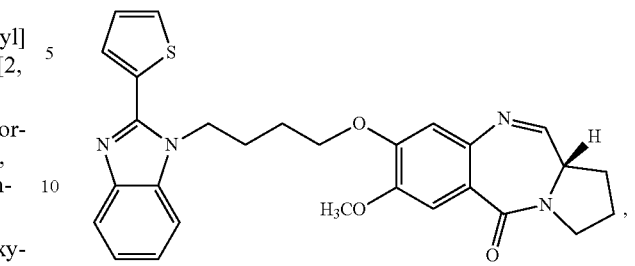

8f
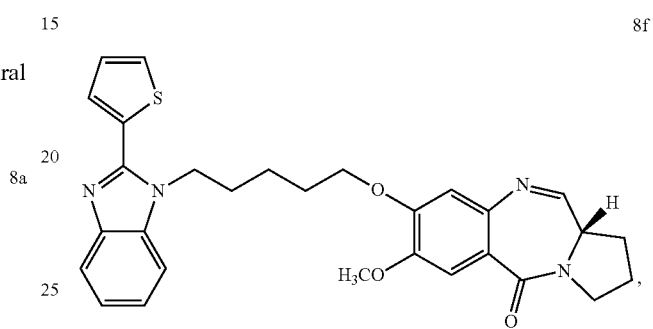

8g
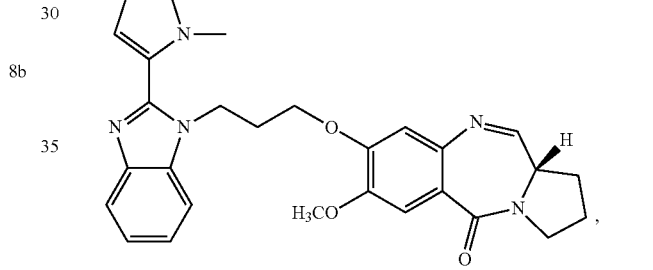

11a

11b
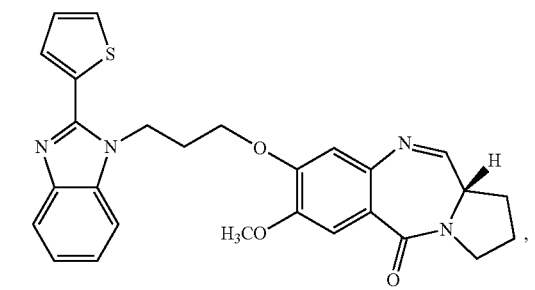

31

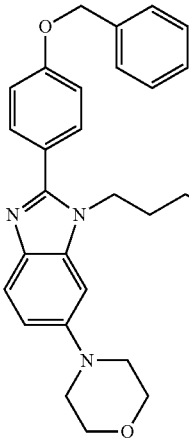, or

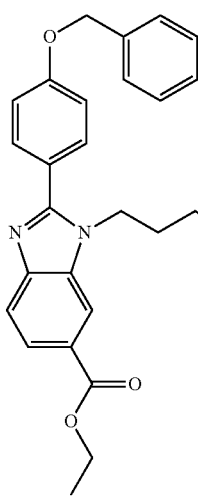.

4. A pharmaceutical composition comprising a compound of claim 1, its analogues, salts or mixture thereof optionally with pharmaceutically acceptable carriers, adjuvants and additives.

5. A process for the preparation of compounds of formula:

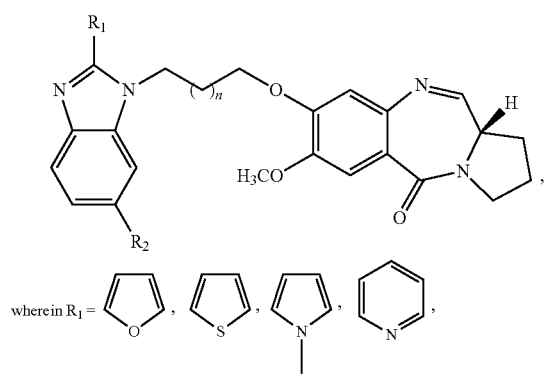

wherein $R_1$ =

32

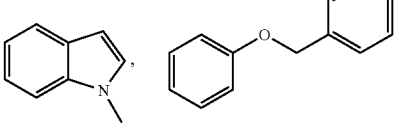

$R_2$ = H, $CO_2Et$, morpholine, and n = 1, 2 and 3 and the said process comprising the steps of:
a) reacting (2S)—N-[4-(n-bromoalkyl)-oxy-5-methoxy-2-nitrobenzoyl]pyrrolidine-2-carboxaldehyde diethylthioacetal of formula 2a-c with benzimidazole compounds of formula 3a-c, or 4a-c, isolating (2S)—N-{4-(n-[2-(2-furyl)benzimidazol-1-yl]alkyl)oxy-5-methoxy-2-nitro benzoyl}pyrrolidine-2-carboxaldehyde diethyl thio acetal/(2S)—N-{4-(n-[2-(2-thienyl)benzimidazol-1-yl]alkyl)oxy-5-methoxy-2-nitro benzoyl}pyrrolidine-2-carboxaldehyde diethyl thioacetal/(2S)—N-{4-(n-[2-(1-methyl-2-pyrrolyl)benzimidazol-1-yl]alkyl)oxy-5-methoxy-2-nitrobenzoyl}pyrrolidine-2-carboxaldehyde diethyl thioacetal of formula 6a-g or (2S)—N-{4-(n-[2-(2-pyridyl)benzimidazol-1-yl]alkyl)oxy-5-methoxy-2-nitrobenoyl}pyrrolidine-2-carboxaldehyde diethyl thioacetal/(2S)—N-{4-(n-[2-[(4-(benzyloxy)phenyl)-6-morpholino]benzimidazol-1-yl]alkyl)-oxy-5-methoxy-2-nitrobenzoyl}pyrrolidine-2-carboxaldehyde diethyl thioacetal/Ethyl-2-[4-(benzyloxy)phenyl]-{[n-[4-(2S)—N-pyrrolidine-2-carboxaldehyde diethylthioacetal]alkyl]-2-methoxy-5-nitrophenoxy}benzimidazol-6-carboxylate of formula 9a-d, respectively;
b) reducing the above nitro compounds of formula 6a-g, or 9a-d with $SnCl_2.2H_2O$, in presence of organic solvent selected from methanol and ethanol up to a reflux temperature, isolating the (2S)—N-{4-(n-[2-(2-furyl)benzimidazol-1-yl]alkyl)oxy-5-methoxy-2-aminobenzoyl}pyrrolidine-2-carboxaldehyde diethyl thioacetal/(2S)—N-{4-(n-[2-(2-thienyl)benzimidazol-1-yl]alkyl)oxy-5-methoxy-2-amino benzoyl}pyrrolidine-2-carboxaldehyde diethyl thioacetal/(2S)—N-{4-(n-[2-(1-methyl-2-pyrrolyl)benzimidazol-1-yl]alkyl)oxy-5-methoxy-2-aminobenzoyl}pyrrolidine-2-carboxaldehyde diethyl thioacetal of formula 7a-g, or (2S)—N-{4-(n-[2-(2-pyridyl)benzimidazol-1-yl]alkyl)oxy-5-methoxy-2-aminobenoyl}pyrrolidine-2-carboxaldehyde diethyl thioacetal/(2S)—N-{4-(n-[2-[(4-(benzyloxy)phenyl)-6-morpholino]benzimidazol-1-yl]alkyl)-oxy-5-methoxy-2-aminobenzoyl}pyrrolidine-2-carboxaldehyde diethyl thioacetal/Ethyl-2-[4-(benzyloxy)phenyl]-{[n-[4-(2S)—N-pyrrolidine-2-carboxaldehyde diethyl thioacetal]alkyl]-2-methoxy-5-amino phenoxy}benzimidazol-6-carboxylate of formula 10a-d, respectively; and
c) reacting the above amino compounds of formula 7a-g, or 10a-d with mercurous chloride and calcium carbonate by known method to obtain the desired compounds of formula 8a-g, or 11a-d, respectively.

6. A method for inhibiting the growth of cancer cells comprising contacting the cancer cells with a compound of claim 1, wherein the cancer cells are selected from the group consisting of leukemia, non-small-cell lung cancer, colon cancer, melanoma, ovarian cancer, prostate cancer, and breast cancer cells.

7. A method for treating cancer comprising contacting cancer cells of the cancer with a compound of claim 1, wherein the cancer is selected from the group consisting of leukemia, non-small-cell lung cancer, colon cancer, melanoma, ovarian cancer, prostate cancer, and breast cancer.

8. The compound of formula:

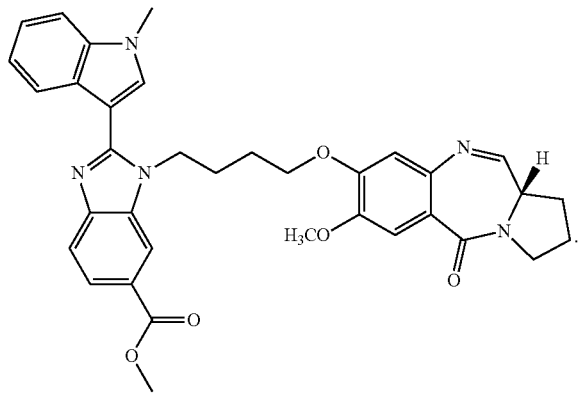

14

9. A pharmaceutical composition comprising a compound of claim 8, its analogues, salts or mixture thereof optionally with pharmaceutically acceptable carriers, adjuvants and additives.

10. A process for making the compound of claim 8 represented by formula 14 which comprises the steps:
   a) reacting (2S)—N-[4-(n-bromoalkyl)-oxy-5-methoxy-2-nitrobenzoyl]pyrrolidine-2-carboxaldehyde diethylthioacetal of formula 2b with benzimidazole compounds of formula 5, methyl-1-{[4-[4-(2S)—N-pyrrolidine-2-carboxaldehyde diethylthioacetal]butyl]-2-methoxy-5-nitrophenoxy}-2-(1-methyl-3-indolyl)benzimidazol-6-carboxylate of formula 12;
   b) reducing the above nitro compounds of formula 12 with $SnCl_2.2H_2O$, in presence of organic solvent selected from methanol and ethanol up to a reflux temperature, isolating the methyl-1-{[4-[4-(2S)—N-pyrrolidine-2-carboxaldehyde diethylthioacetal]butyl]-2-methoxy-5-aminophenoxy}-2-(1-methyl-3-indolyl)benzimidazol-6-carboxylate of formula 13, and
   c) reacting the above amino compound of formula 13 with mercurous chloride and calcium carbonate by known method to obtain the desired compound of formula 14.

11. A method for inhibiting the growth of cancer cells comprising contacting the cancer cells with the compound of claim 3, wherein the cancer cells are selected from the group consisting of leukemia, non-small-cell lung cancer, colon cancer, melanoma, ovarian cancer, prostate cancer, and breast cancer cells.

12. A method for inhibiting the growth of cancer cells comprising contacting the cancer cells with the compound of claim 8, wherein the cancer cells are selected from the group consisting of leukemia, non-small-cell lung cancer, colon cancer, melanoma, ovarian cancer, prostate cancer, and breast cancer cells.

13. A method for treating cancer comprising contacting cancer cells of the cancer with the compound of claim 3, wherein the cancer is selected from the group consisting of leukemia, non-small-cell lung cancer, colon cancer, melanoma, ovarian cancer, prostate cancer, and breast cancer.

14. A method for treating cancer comprising contacting cancer cells of the cancer with the compound of claim 8, wherein the cancer is selected from the group consisting of leukemia, non-small-cell lung cancer, colon cancer, melanoma, ovarian cancer, prostate cancer, and breast cancer.

* * * * *